(12) United States Patent
Sauer

(10) Patent No.: US 8,652,149 B2
(45) Date of Patent: *Feb. 18, 2014

(54) VASCULAR HOLE CLOSURE

(75) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 1266 days.

This patent is subject to a terminal disclaimer.

(21) Appl. No.: 10/056,473

(22) Filed: Jan. 23, 2002

(65) Prior Publication Data

US 2002/0123756 A1    Sep. 5, 2002

Related U.S. Application Data

(63) Continuation of application No. 09/041,207, filed on Mar. 12, 1998, now Pat. No. 6,368,334, which is a continuation of application No. 08/734,159, filed on Oct. 21, 1996, now Pat. No. 5,766,183.

(51) Int. Cl.
   *A61B 17/10*    (2006.01)
(52) U.S. Cl.
   USPC .......................................... 606/139
(58) Field of Classification Search
   USPC .......................... 606/139, 144, 148
   See application file for complete search history.

(56) References Cited

U.S. PATENT DOCUMENTS

| | | | |
|---|---|---|---|
| 2,092,929 A | 9/1937 | Ovington | 223/102 |
| 3,361,382 A | 1/1968 | Converse | |
| 3,612,050 A | 10/1971 | Sheridan | 128/214.4 |
| 3,802,438 A | 4/1974 | Wolvek | 128/335 |
| 3,901,244 A | 8/1975 | Schweizer | |
| 3,929,123 A | 12/1975 | Jamshidi | 128/2 B |
| 4,102,478 A | 7/1978 | Samoilov | |
| 4,134,406 A | 1/1979 | Iglesias | |
| 4,662,068 A | 5/1987 | Polonsky | 30/124 |
| 4,667,684 A | 5/1987 | Leigh | 128/754 |
| 4,719,713 A | 1/1988 | Hagle | |
| 4,779,616 A | 10/1988 | Johnson | |
| 4,852,568 A | 8/1989 | Kensey | 128/325 |
| 4,890,612 A | 1/1990 | Kensey | 606/213 |
| 4,892,098 A | 1/1990 | Sauer | 606/18 |
| 4,917,082 A | 4/1990 | Grossi et al. | |
| 4,929,240 A | 5/1990 | Kirsch et al. | 606/151 |
| 5,137,198 A | 8/1992 | Nobis et al. | |
| 5,211,644 A | 5/1993 | VanBeek et al. | 606/1 |

(Continued)

FOREIGN PATENT DOCUMENTS

| CA | 667514 | 7/1963 |
|---|---|---|
| WO | WO0135833 | 5/2001 |

OTHER PUBLICATIONS

Application No. 200880014925.4 First Office Action dated Aug. 12, 2010, 10 pages.

(Continued)

*Primary Examiner* — Gary Jackson
*Assistant Examiner* — Lindsey Bachman
(74) *Attorney, Agent, or Firm* — Cantor Colburn LLP

(57) ABSTRACT

A method and apparatus for closing a punctured blood vessel is described. The apparatus includes a suturing instrument adapted to apply at least one suture to at least a portion of a blood vessel in order to close a puncture wound therein. In a preferred embodiment, the suture is secured by crimping a sleeve member over the free ends of the suture with a crimping instrument.

31 Claims, 20 Drawing Sheets

(56) References Cited

U.S. PATENT DOCUMENTS

| | | | | |
|---|---|---|---|---|
| 5,242,459 | A | 9/1993 | Buelna | |
| 5,261,918 | A | 11/1993 | Phillips et al. | 606/140 |
| 5,304,184 | A | 4/1994 | Hathaway et al. | 606/144 |
| 5,306,280 | A | 4/1994 | Bregen et al. | |
| 5,336,229 | A | 8/1994 | Noda | |
| 5,342,393 | A | 8/1994 | Stack | 606/213 |
| 5,368,601 | A | 11/1994 | Sauer et al. | 606/144 |
| 5,370,660 | A | 12/1994 | Weinstein et al. | 606/215 |
| 5,380,290 | A | 1/1995 | Makower et al. | 604/164 |
| 5,382,254 | A * | 1/1995 | McGarry et al. | 606/143 |
| 5,383,901 | A | 1/1995 | McGregor et al. | 606/223 |
| 5,391,183 | A | 2/1995 | Janzen et al. | |
| 5,405,354 | A | 4/1995 | Sarrett | 606/148 |
| 5,409,478 | A * | 4/1995 | Gerry et al. | 606/1 |
| 5,411,520 | A | 5/1995 | Nash et al. | 606/213 |
| 5,417,699 | A | 5/1995 | Klein et al. | 606/144 |
| 5,417,700 | A | 5/1995 | Egan | 606/144 |
| 5,423,830 | A | 6/1995 | Schneebaum et al. | |
| 5,425,737 | A | 6/1995 | Burbank et al. | 606/144 |
| 5,425,745 | A * | 6/1995 | Green et al. | 606/219 |
| 5,431,666 | A * | 7/1995 | Sauer et al. | 606/139 |
| 5,437,665 | A | 8/1995 | Munro | |
| 5,454,822 | A | 10/1995 | Schob et al. | 606/148 |
| 5,466,241 | A | 11/1995 | Leroy et al. | |
| 5,476,470 | A | 12/1995 | Fitzgibbons, Jr. | 606/144 |
| 5,478,003 | A | 12/1995 | Green et al. | |
| 5,486,186 | A | 1/1996 | Yoon | 606/148 |
| 5,501,692 | A | 3/1996 | Riza | |
| 5,520,702 | A | 5/1996 | Sauer et al. | |
| 5,527,319 | A | 6/1996 | Green et al. | 606/143 |
| 5,527,322 | A | 6/1996 | Klein et al. | |
| 5,533,987 | A | 7/1996 | Pray et al. | 604/280 |
| 5,540,698 | A | 7/1996 | Preissman | 606/103 |
| 5,554,169 | A * | 9/1996 | Green et al. | 606/219 |
| 5,562,664 | A | 10/1996 | Durlacher et al. | |
| 5,562,685 | A | 10/1996 | Mollenauer et al. | |
| 5,562,686 | A * | 10/1996 | Sauer et al. | 606/144 |
| 5,575,800 | A | 11/1996 | Gordon | 606/144 |
| 5,575,801 | A | 11/1996 | Habermeyer et al. | |
| 5,578,057 | A | 11/1996 | Wenstrom, Jr. | |
| 5,586,986 | A | 12/1996 | Hinchliffe | 606/147 |
| 5,591,177 | A | 1/1997 | Lehrer | 606/139 |
| 5,643,289 | A | 7/1997 | Sauer et al. | |
| 5,665,105 | A * | 9/1997 | Furnish et al. | 606/205 |
| 5,669,917 | A | 9/1997 | Sauer et al. | |
| 5,676,689 | A | 10/1997 | Kensey et al. | 606/213 |
| 5,700,273 | A | 12/1997 | Buelna et al. | |
| 5,704,973 | A | 1/1998 | Sakurada et al. | 117/15 |
| 5,718,714 | A | 2/1998 | Livneh | 606/205 |
| 5,725,536 | A | 3/1998 | Oberlin et al. | |
| 5,752,964 | A | 5/1998 | Mericle | 606/148 |
| 5,766,183 | A | 6/1998 | Sauer | 606/139 |
| 5,772,663 | A | 6/1998 | Whiteside et al. | 606/74 |
| 5,782,844 | A | 7/1998 | Yoon et al. | |
| 5,792,152 | A * | 8/1998 | Klein et al. | 606/144 |
| 5,792,153 | A | 8/1998 | Swain et al. | 606/144 |
| 5,797,927 | A | 8/1998 | Yoon | |
| 5,800,447 | A | 9/1998 | Wenstrom, Jr. | |
| 5,810,849 | A | 9/1998 | Kontos | 606/144 |
| 5,814,065 | A * | 9/1998 | Diaz | 606/213 |
| 5,830,125 | A | 11/1998 | Scribner et al. | |
| 5,836,955 | A | 11/1998 | Buelna et al. | 606/148 |
| 5,836,956 | A | 11/1998 | Buelna et al. | |
| 5,839,639 | A | 11/1998 | Sauer et al. | 227/175.1 |
| 5,855,585 | A * | 1/1999 | Kontos | 606/144 |
| 5,935,149 | A | 8/1999 | Ek | |
| 5,938,668 | A * | 8/1999 | Scirica et al. | 606/145 |
| 5,997,555 | A | 12/1999 | Kontos | |
| 6,036,699 | A * | 3/2000 | Andreas et al. | 606/139 |
| 6,045,560 | A | 4/2000 | McKean et al. | |
| 6,048,358 | A | 4/2000 | Barak | |
| 6,056,771 | A | 5/2000 | Proto | 606/222 |
| 6,068,648 | A | 5/2000 | Cole et al. | |
| 6,099,553 | A | 8/2000 | Hart et al. | |
| 6,117,144 | A * | 9/2000 | Nobles et al. | 606/144 |
| 6,136,010 | A | 10/2000 | Modesitt et al. | |
| 6,206,893 | B1 | 3/2001 | Klein et al. | |
| 6,217,592 | B1 | 4/2001 | Freda et al. | |
| 6,221,084 | B1 | 4/2001 | Fleenor | 606/148 |
| 6,254,620 | B1 | 7/2001 | Koh et al. | |
| 6,368,334 | B1 | 4/2002 | Sauer | |
| 6,398,796 | B2 | 6/2002 | Levinson | 606/144 |
| 6,428,549 | B1 | 8/2002 | Kontos | |
| 6,436,109 | B1 | 8/2002 | Kontos | 606/148 |
| 6,451,031 | B1 | 9/2002 | Kontos | 606/144 |
| 6,454,777 | B1 | 9/2002 | Green | 606/144 |
| 6,511,489 | B2 | 1/2003 | Field et al. | 606/148 |
| 6,514,263 | B1 | 2/2003 | Stefanchik et al. | 606/144 |
| 6,517,553 | B2 * | 2/2003 | Klein et al. | 606/144 |
| 6,533,796 | B1 | 3/2003 | Sauer et al. | |
| 6,569,187 | B1 | 5/2003 | Bonutti et al. | |
| 6,641,592 | B1 | 11/2003 | Sauer et al. | 606/144 |
| 6,830,174 | B2 | 12/2004 | Hillstead et al. | |
| 6,997,931 | B2 | 2/2006 | Sauer et al. | |
| 7,037,315 | B2 | 5/2006 | Sancoff et al. | |
| 2002/0099389 | A1 | 7/2002 | Michler et al. | |
| 2002/0177860 | A1 | 11/2002 | Nicholas et al. | |
| 2003/0040760 | A1 | 2/2003 | Hnojewyj et al. | |
| 2003/0050650 | A1 | 3/2003 | Field et al. | |
| 2003/0204205 | A1 | 10/2003 | Sauer et al. | |
| 2004/0068272 | A1 | 4/2004 | Sauer et al. | |
| 2008/0082123 | A1 | 4/2008 | Forsberg et al. | |
| 2010/0217311 | A1 | 8/2010 | Jenson et al. | |

OTHER PUBLICATIONS

Application No. 200880014925.4 Second Office Action dated Jun. 15, 2011, 6 pages.
International Search Report for PCT/US02/33747 dated Mar. 7, 2003, 3 pages.
International Search Report and Written Opinion for PCT/US2008/059551 dated Sep. 25, 2008, 8 pages.
International Search Report and Written Opinion for PCT/US2010/039328 dated Feb. 8, 2011, 16 pages.
China Application No. 200880014925.4 Third Office Action dated Nov. 9, 2011, 5 pages.
Supplemental European Search Report for PCT/US0233747 dated Feb. 26, 2008, 5 pages.

* cited by examiner

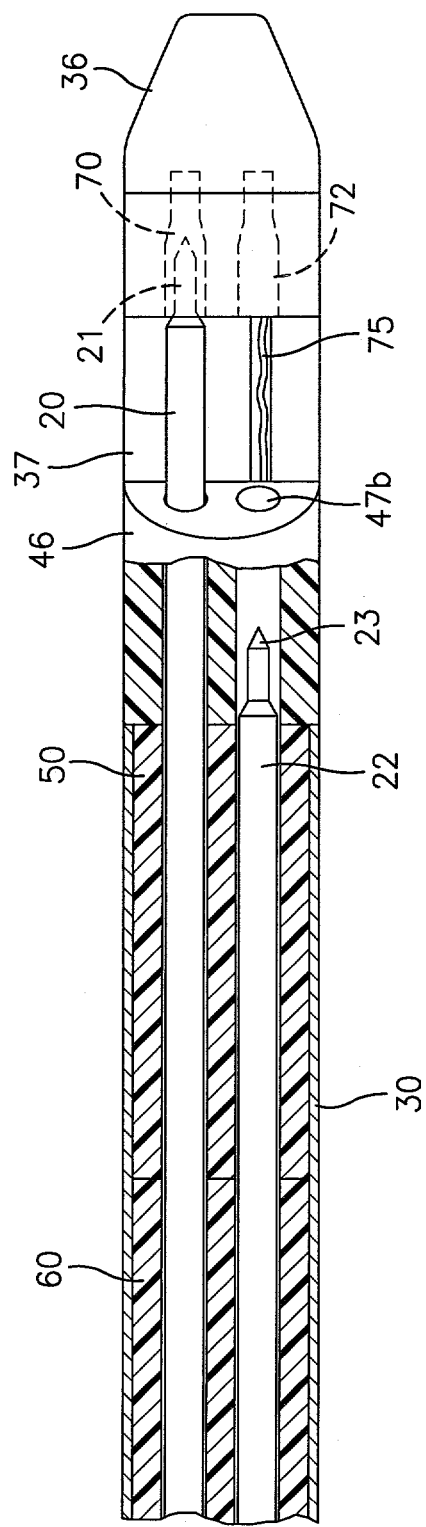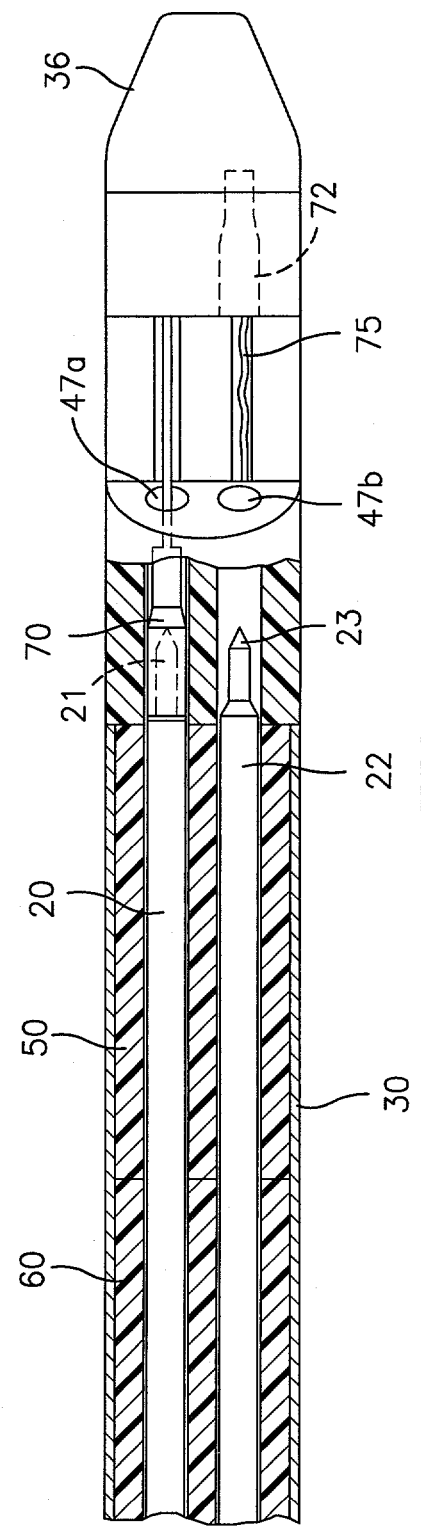

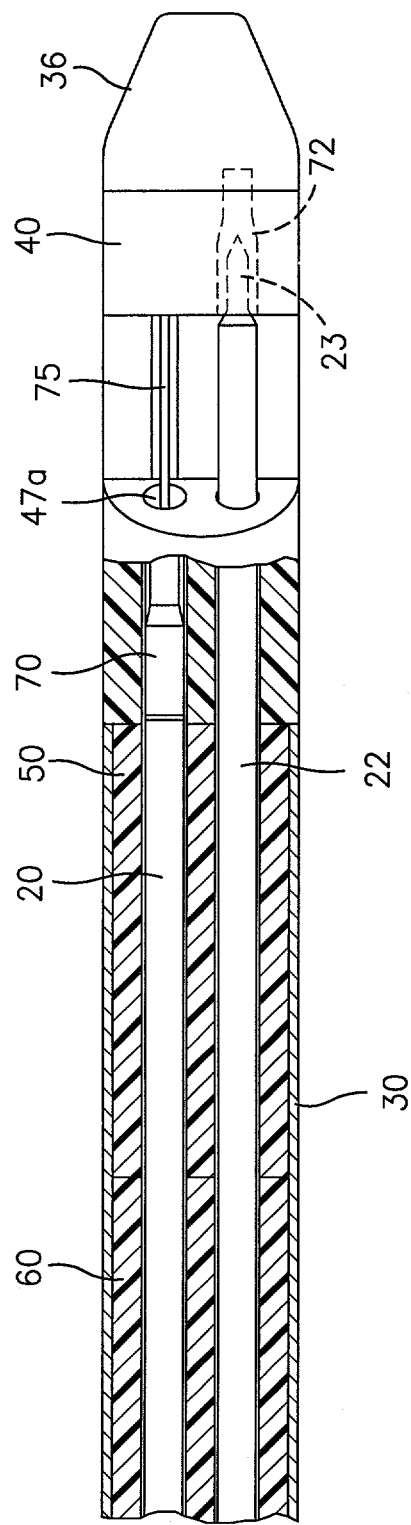
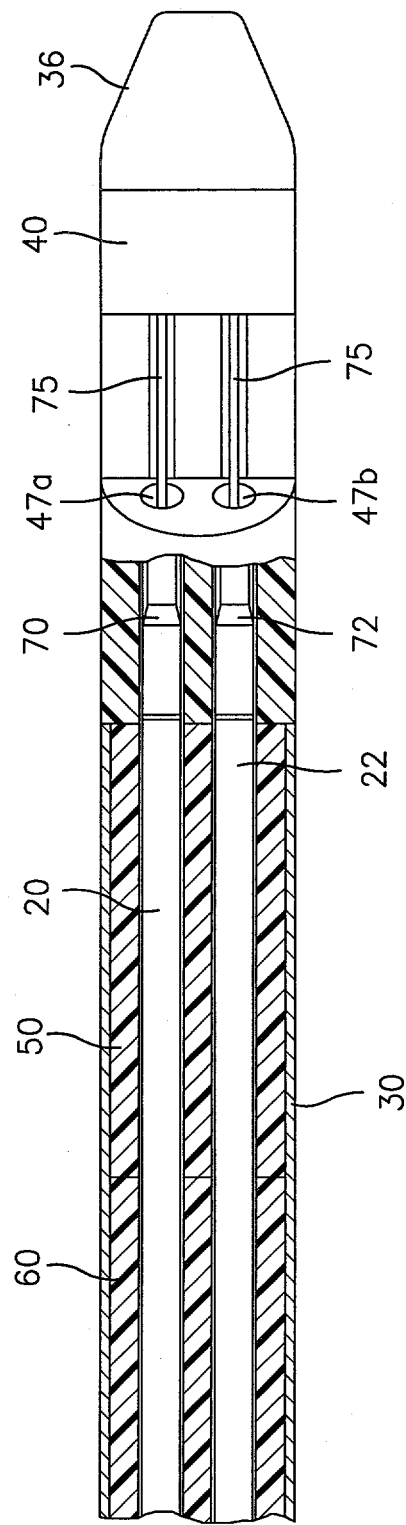
FIG. 11A
FIG. 12

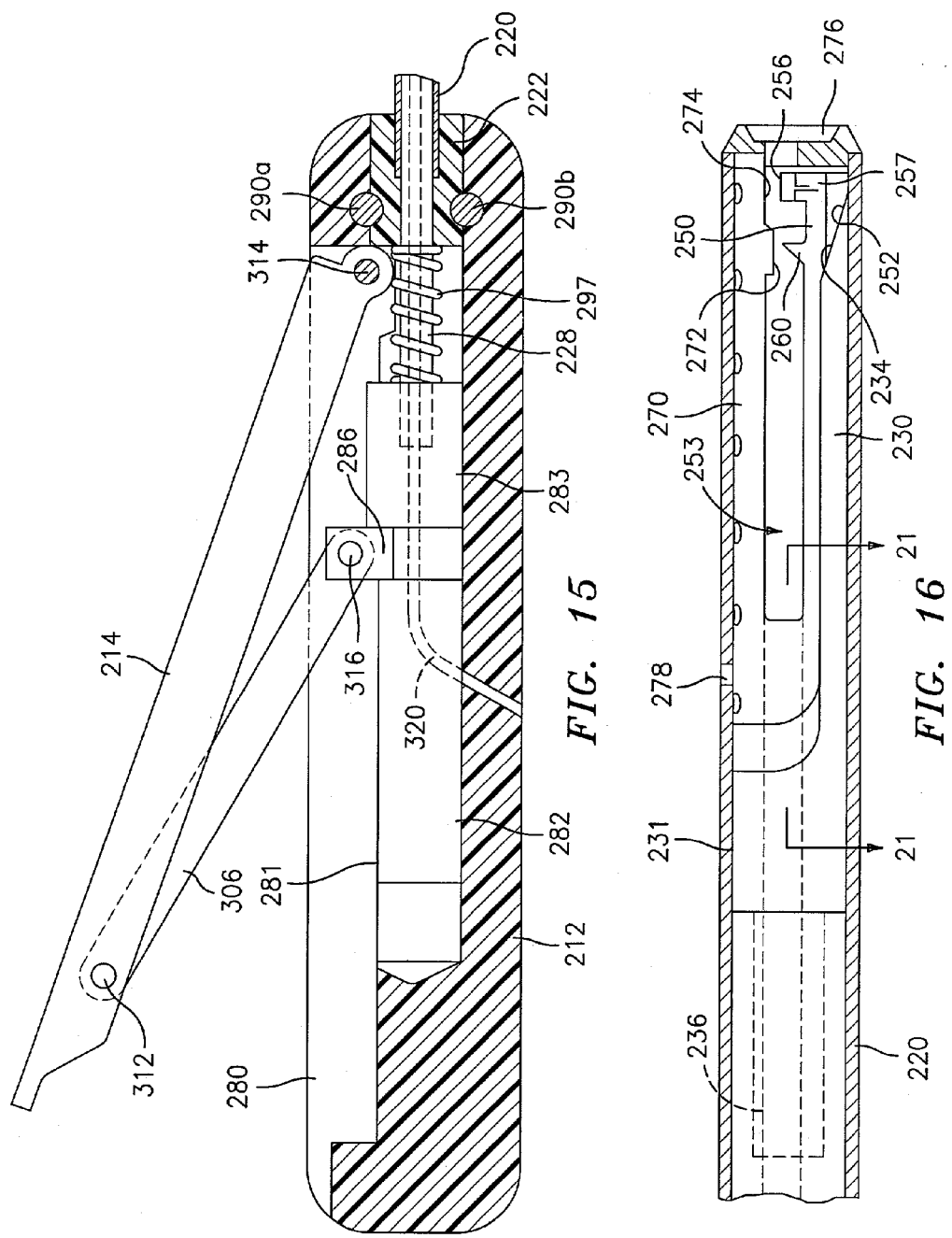

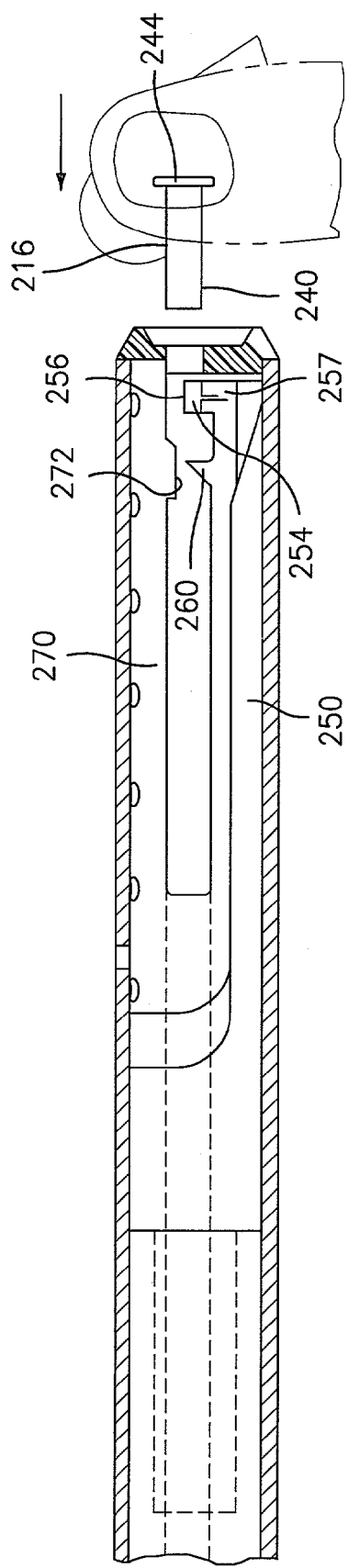
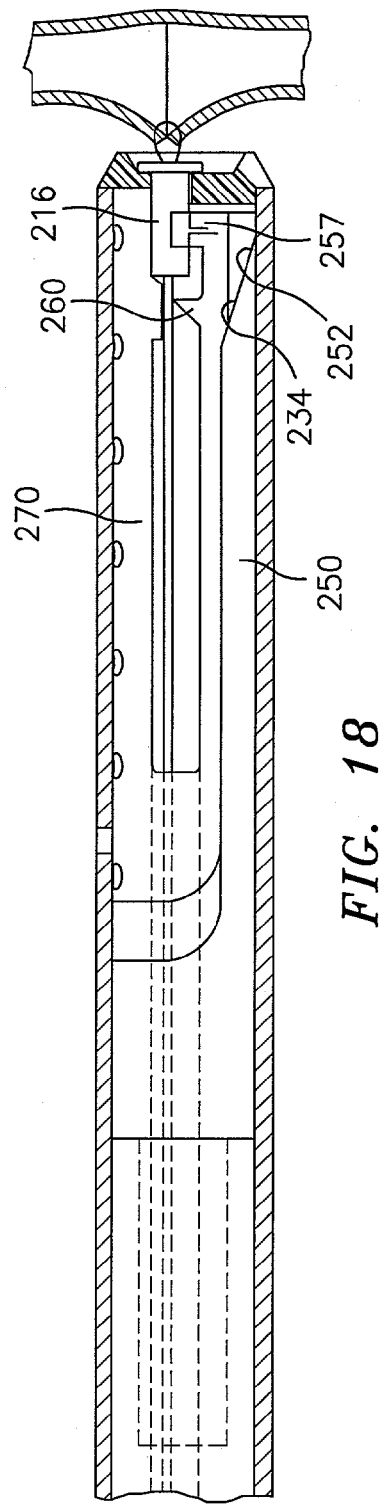
FIG. 17
FIG. 18

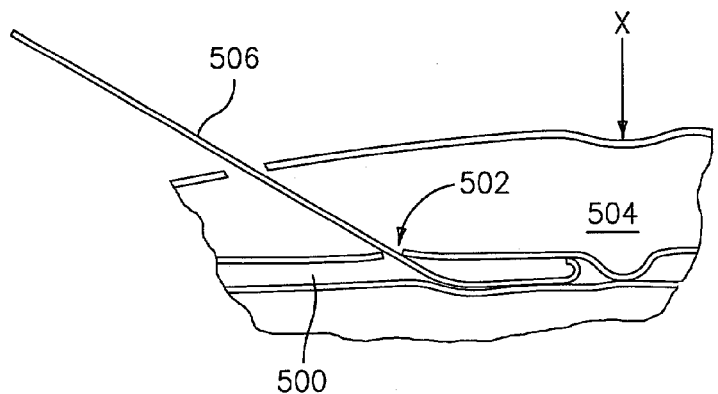
FIG. 24
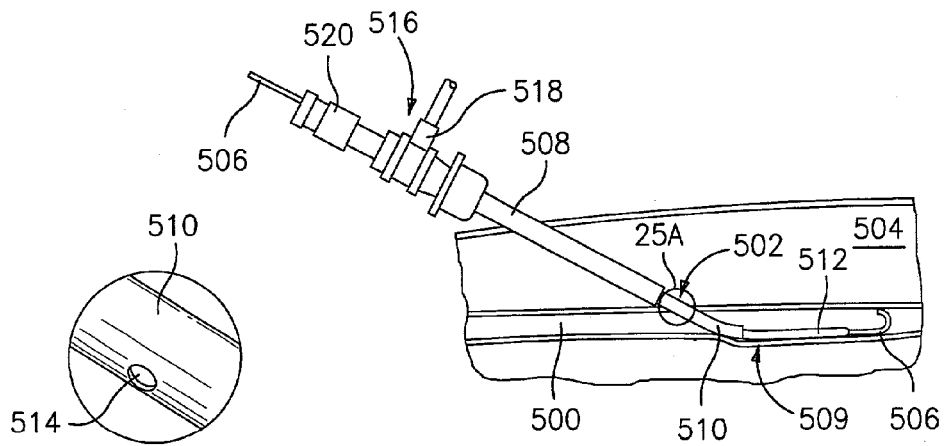
FIG. 25A
FIG. 25
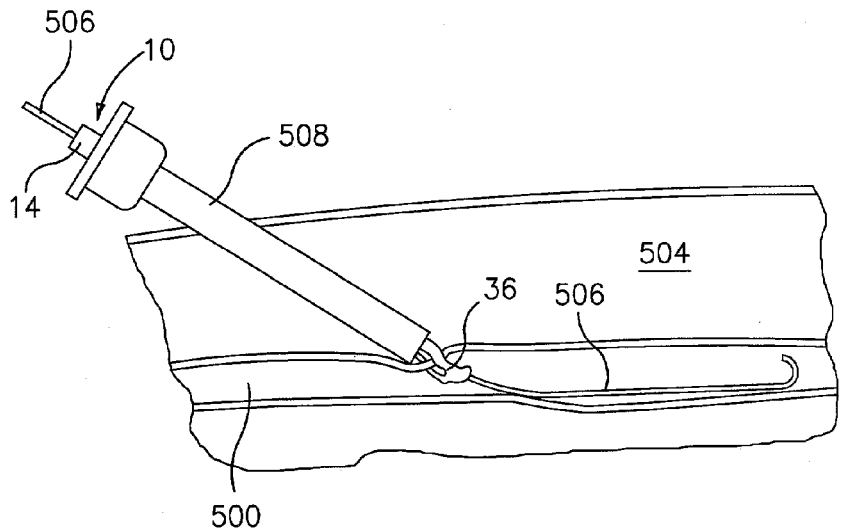
FIG. 26

VASCULAR HOLE CLOSURE

CROSS REFERENCE TO RELATED APPLICATIONS

This application is a continuation of U.S. patent application Ser. No. 09/041,207, filed on Mar. 12, 1998, now U.S. Pat. No. 6,368,334 which has been allowed, which is a continuation of U.S. patent application Ser. No. 08/734,159, filed on Oct. 21, 1996, now U.S. Pat. No. 5,766,183.

BACKGROUND OF THE INVENTION

The present disclosure relates to instruments and a method for closing a hole or puncture in a blood vessel. More particularly, this disclosure relates to applying at least one suture to close a hole in a blood vessel after an intravascular catheterization procedure.

When performing catheterization procedures, such an angiography or angioplasty, a catheter is generally introduced into the vascular system by first penetrating the skin, underlying muscle tissue and blood vessel with a sharpened hollow needle. Next, a guide wire is commonly inserted through the lumen of the hollow needle and is caused to enter the selected blood vessel. Subsequently, the needle is typically slid off the guide wire and a combination of a dilator and an introducer (or an introducer alone) are fed over the guide wire and pushed through the skin to enter the vessel. The guide wire can then be removed and the desired catheter to carry out the procedure is fed through the lumen of the introducer and advanced through the vascular system until the working end of the catheter is appropriately positioned. Following the conclusion of the catheterization procedure, the working catheter will be withdrawn and, subsequently, the dilator and/or introducer will also be removed from the wound.

At this point in the procedure, the vessel leakage must be controlled in order to stem the flow of blood through the puncture. Because it is common practice to administer a blood thinning agent to the patient prior to many of the catheterization procedures, stemming the blood flow can be troublesome. A common method of sealing the wound is to maintain external pressure over the vessel until the puncture naturally seals. This method of puncture closure typically takes about thirty minutes, with the length of time usually being greater if the patient is hypertensive or anti-coagulated. In some anti-congulated patients, the introducer is left in place for hours to allow the anti-coagulant to wear off. When human hand pressure is utilized, it can be uncomfortable for the patient and can use costly professional time on the part of the hospital staff. Other pressure techniques, such as pressure bandages, sandbags or clamps, have been employed, but these devices also require the patient to remain motionless for an extended period of time and the patient must be closely monitored to ensure their effectiveness.

Other devices have been disclosed which plug or otherwise provide an obstruction in the area of the puncture. See, for example, U.S. Pat. Nos. 4,852,568 and 4,890,612, wherein a collagen plug is disposed in the blood vessel opening. When the plug is exposed to body fluids, it swells to create a block for the wound in the vessel wall. A potential problem of plugs introduced into the vessel is that particles may break off and float downstream to the point where they may lodge in a smaller vessel, causing an infarct to occur. Collagen material also acts as a nidus for platelet aggregation and, therefore, can cause intraluminal deposition of hemostatic agent, thereby creating the possibility of a thrombosis at the puncture sight.

Other plug-like devices are disclosed, for example, in U.S. Pat. Nos. 5,342,393, 5,370,660 and 5,411,520.

Surgical clips and clip appliers are known have also been used in vascular surgery, particularly to join severed vessels. See, for example, U.S. Pat. No. 4,929,240 (Kirsch, et al). The clips disclosed in the '240 Patent are generally arcuate in shape and have two legs that are biased towards each other by clip applier jaws to capture vessel tissue therebetween. While vascular clips have been successfully used in surgery, the surgical procedures in which the clips are typically used allow the surgeon to view the area to be clipped. In catheter puncture repair procedures, however, the wound is generally not visible, making proper clip application, if attempted, difficult. Commonly assigned U.S. patent application Ser. No. 08/510,834 discloses the use of a guide wire to aid in locating the distal end of a clip applying device.

The use of suturing instruments to close a vessel puncture are disclosed in U.S. Pat. No. 5,417,699 (Klein et al.), wherein one of the instruments has a pair of needles, with the points oriented in a proximal direction, releasably disposed at a distal end thereof. A cannula is used to pass the distal end of the instrument and the needles through a vessel puncture and into the vessel. Once in the vessel, the cannula is moved in a proximal direction to expose the needles. Thereafter, proximal movement of the instrument causes the needles to pass through the vessel wall (from the inside to the outside) on either side of the vessel puncture and the needles are withdrawn. A strand of suture material secured between the blunt ends of the needles is also drawn through the needle puncture holes, thereby leaving a span of suture across the hole on the inside of the vessel. The suture can then be tied to close the vascular puncture. A disadvantage to this approach is the traumatic step of passing the cannula and distal end of the suturing instrument through the vascular hole and then exposing sharp needle tips within the vessel. Also, the instruments disclosed in the '699 Patent are relatively complex and may be unreliable in some vessels and costly to manufacture.

Another suturing instrument is disclosed in U.S. Pat. No. 5,431,666 (Sauer et al.). The Sauer '666 instrument uses a pair of longitudinally movable needles to pick up corresponding ferrules at a distal end of the instrument. The ferrules have a strand of suture material disposed therebetween and are initially separated from the needles by a gap in the instrument. In use, tissue to be sutured is disposed in the gap between the needles and ferrules. A first needle punctures the tissue, engages a ferrule and draws the ferrule back through the tissue. The instrument can then be relocated to another portion of tissue and the second needle is actuated to pick up and draw the second ferrule therethrough. The suture material can then be tied or otherwise cinched in place to secure the tissue portions. When using the device disclosed in Sauer et al. '666, the surgeon is typically able to view the surgical site.

Therefore, there is a need for surgical techniques and instrumentation suitable for dosing punctures in blood vessels, particularly those created during catheterization procedures. This need requires a reliable hemeostasis of the puncture in a quick and efficient manner with minimal trauma the surrounding vascular tissue. The instrumentation must also allow the user to close the puncture without directly viewing the punctured site.

BRIEF DESCRIPTION OF THE DRAWINGS

Various embodiments of the surgical apparatus of the subject application will be described herein below with reference to the drawings, wherein:

FIG. 9A is a view similar to FIG. 4B corresponding to the position of the levers in FIG. 9 and illustrating the first needle engaged with the ferrule and the second needle in the retracted position;

FIG. 10 is a view similar to FIG. 9A illustrating the first needle in the retracted position after engagement with the ferrule;

FIG. 11A is a view similar to FIG. 4B corresponding to the position of the levers in FIG. 11 and illustrating advancement of the second needle into engagement with the ferrule;

FIG. 12 is a view similar to FIG. 4B illustrating the first and second needles in the retracted position after engagement with their respective ferrules;

FIG. 15 is a longitudinal cross-sectional view of the body portion of the apparatus of FIG. 13 illustrating the lever in the initial (open) position;

FIG. 16 is a longitudinal cross-sectional view of the tubular portion of the apparatus corresponding to the position of the lever in FIG. 15 and illustrating the jaws in the open position;

FIG. 17 is a cross-sectional view similar to FIG. 16 illustrating the suture securing member being loaded into the tubular portion of the apparatus;

FIG. 18 is a cross-sectional view similar to FIG. 17 illustrating the suture securing member loaded in the tubular portion of the apparatus;

FIG. 24 is a cross-sectional view of a blood vessel and surrounding tissue illustrating a guide wire disposed within the blood vessel;

FIG. 25 is a view similar to FIG. 24 illustrating a cannula and obturator assembly disposed over the guide wire;

FIG. 25A is an enlarged view of a portion of the obturator assembly of FIG. 25 illustrating an aspiration port;

FIG. 26 is a cross-sectional view of a blood vessel and surrounding tissue illustrating the surgical suturing apparatus of FIG. 1 passing through a cannula and applying a suture adjacent the inferior side of the vessel puncture wound;

DETAILED DESCRIPTION OF THE PREFERRED EMBODIMENTS

Figure 1:
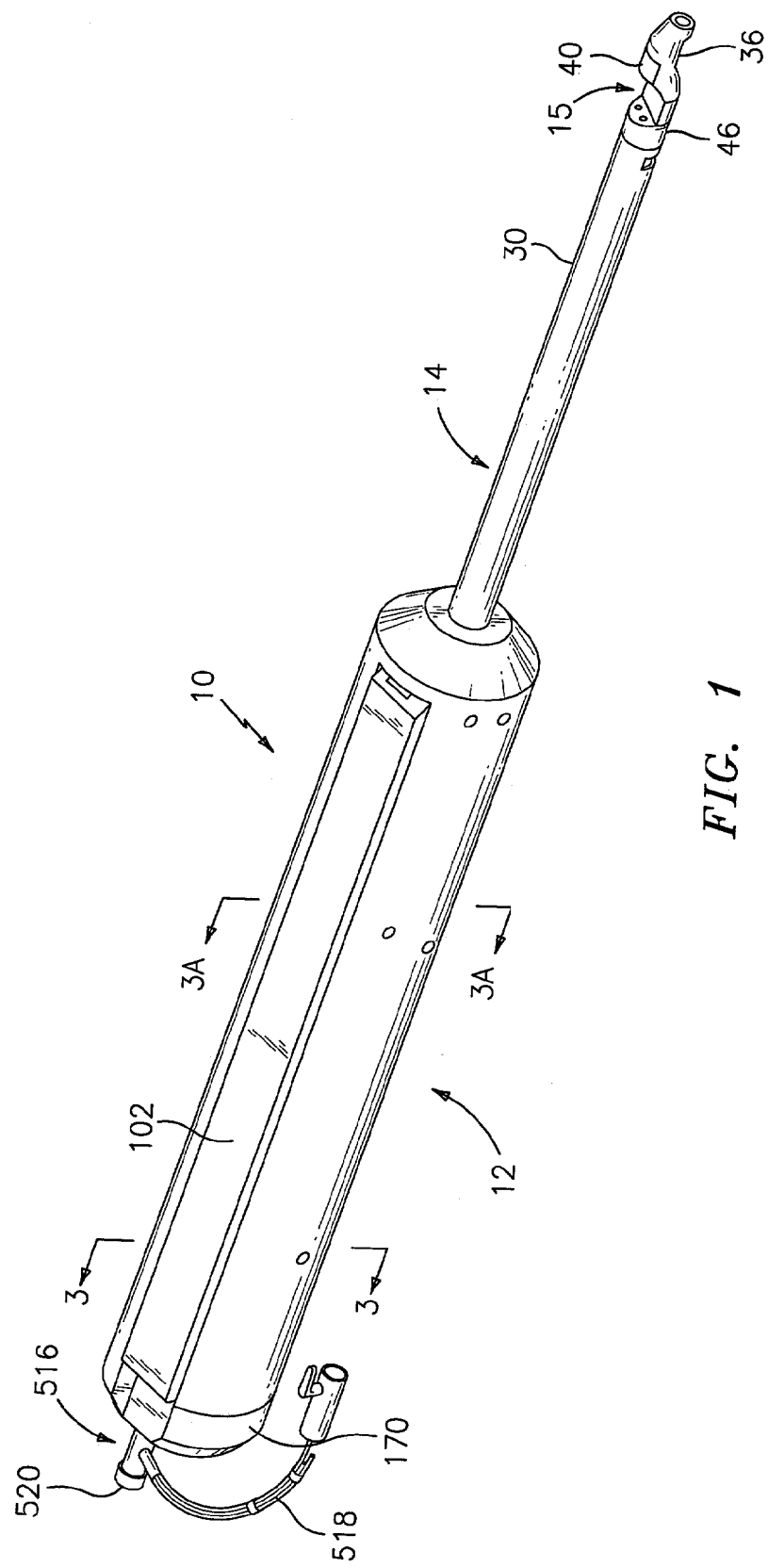
FIG. 1 is a perspective view of the apparatus for suturing body tissue.

Referring now to the drawings, wherein like reference numerals identify similar or identical elements throughout the several views, an apparatus for applying a suture to body tissue is illustrated in FIGS. 1-12 and is designated generally by reference numeral 10. Another apparatus is also disclosed, designated by reference numeral 200 and illustrated in FIGS. 13-23, for applying a connecting sleeve around the suture after it has been applied to the body tissue by apparatus 10 in order to secure the suture. Note that the terms first and "second" as used herein are for the reader's convenience and should not be interpreted as necessarily denoting the order in which the components are actuated.

Figure 2:
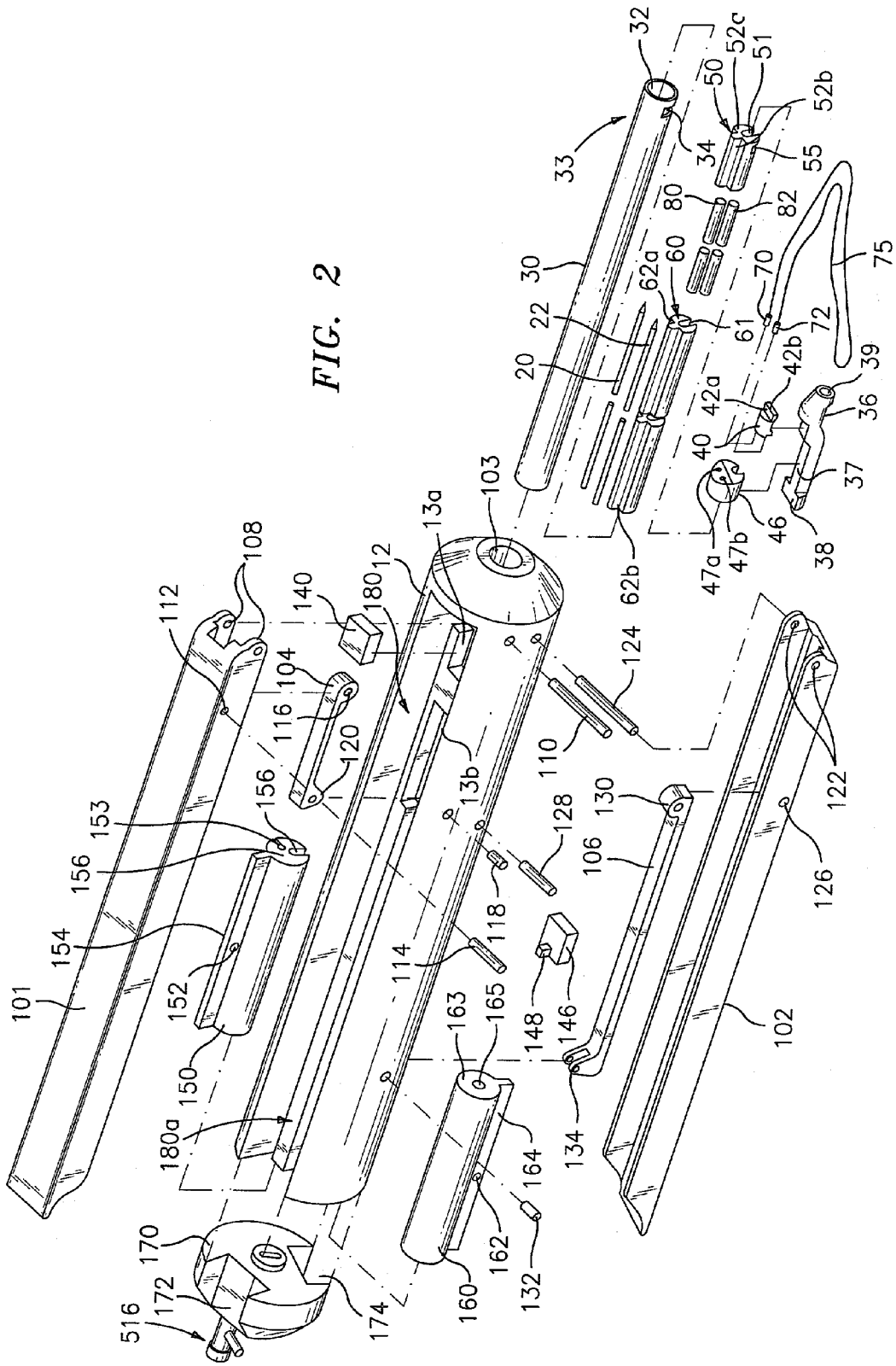
FIG. 2 is an exploded perspective view of the surgical suturing apparatus of FIG. 1.

Turning first to the apparatus 10 for applying a suture, and with particular reference to FIGS. 1 and 2, apparatus 10 includes a body portion 12 and an elongated tubular portion 14 extending from a distal end of the body portion 12. The tubular portion 14 includes a window 15 configured to receive the body tissue to the sutured. Housed within tubular portion 14 are a pair of needles with are advanced by respective levers through the tissue positioned in window 15 and into engagement with ferrules supported at the distal end of the apparatus.

Each ferrule is attached to one end of a suture so that advancement of the needles into engagement with the ferrules effectively engages the suture. Subsequent retraction of the needles into the tubular body portion pulls the suture through the body tissue. This is discussed in detail below.

Turning initially to the tubular portion 14, and with continued reference to FIGS. 1 and 2, tubular portion 14 includes an outer tube 30 having an axial bore 32 dimensioned to receive a proximal needle guide 60 and a distal needle guide 50. Also mounted within outer tube 30, at the distal portion 33, is a face 46 having a first opening 47a to receive first needle 20 and a second opening 47b to receive second needle 22. Openings 47a and 47b are in axial alignment with longitudinal grooves 52a, 52b and 62a, 62b of needle guides 50 and 60, respectively.

Extending from distal end portion 33 of outer tube 30 is a tongue 36 on which mounts a ferrule holder 40. More specifically, tongue 36 includes a base 37 terminating in a T-shaped extension 38 which extends through a notch 55 in distal needle guide 50 and through a notch 34 in outer tube 30 (see also FIGS. 4A and 6) to fixedly mount tongue 36 to outer tube 30 and guide 50. Alternately, the tongue 36 can be brazed to the outer tube. Face 46 is snapped onto base 37 in front of T-extension 38. Ferrule holder 40 has projecting surfaces 41 which sit within correspondingly configured grooves within the tongue 36 as best seen in FIG. 4A. Lip 36a, in conjunction with the projection and groove arrangement, functions to retain ferrule holder 40 on base 37 of tongue 36. Tongue 36 also has a distal opening 39, axially aligned with the central bore 103 of body portion 12, to allow passage of guide wire tube 82 to accommodate a guide wire (not shown in FIG. 2) in order to locate the instrument for the reasons discussed below. Exit opening 39a, formed at a bottom surface of tongue 36 as viewed in FIG. 4A, provides a passageway for radiopaque dye or other medium if injected through guide wire tube 82.

With reference to FIGS. 2, 4A and 12, ferrule holder 40 has a pair of recesses to receive ferrules 70 and 72. These ferrules, as shown, are mounted to opposite ends of the suture 75, and have a central opening dimensioned to frictionally engage sharp tips 21, 23 of needles 20, 22. FIG. 4B shows needles 20, 22 prior to engagement where they are initially spaced from ferrules 70, 72, with the distal tips 21, 23 positioned in openings 47a, 47b of face 46.

When the first needle 20 is advanced by first lever 101 in the manner described below, needle 20 passes through opening 47a and through the body tissue positioned in window 15 into the recess of ferrule holder 46 so that tip 21 frictionally engages ferrule 70 as illustrated in FIG. 9A. Subsequently, when needle 20 is retracted, ferrule 70 is likewise retracted into opening 47a, pulling the portion of suture 75 through the body tissue as shown in FIG. 10. In a similar manner, when needle 22 is advanced by second lever 102, it passes through opening 47b in ferrule holder 46 and through the body tissue so that tip 23 enters the recess of ferrule holder 46 to frictionally engage ferrule 72 as shown in FIG. 11A. When subsequently retracted, needle 22 pulls ferrule 72 through opening 47b in face 46 to pull suture 75 through the body tissue as shown in FIG. 12.

Figure 3A:
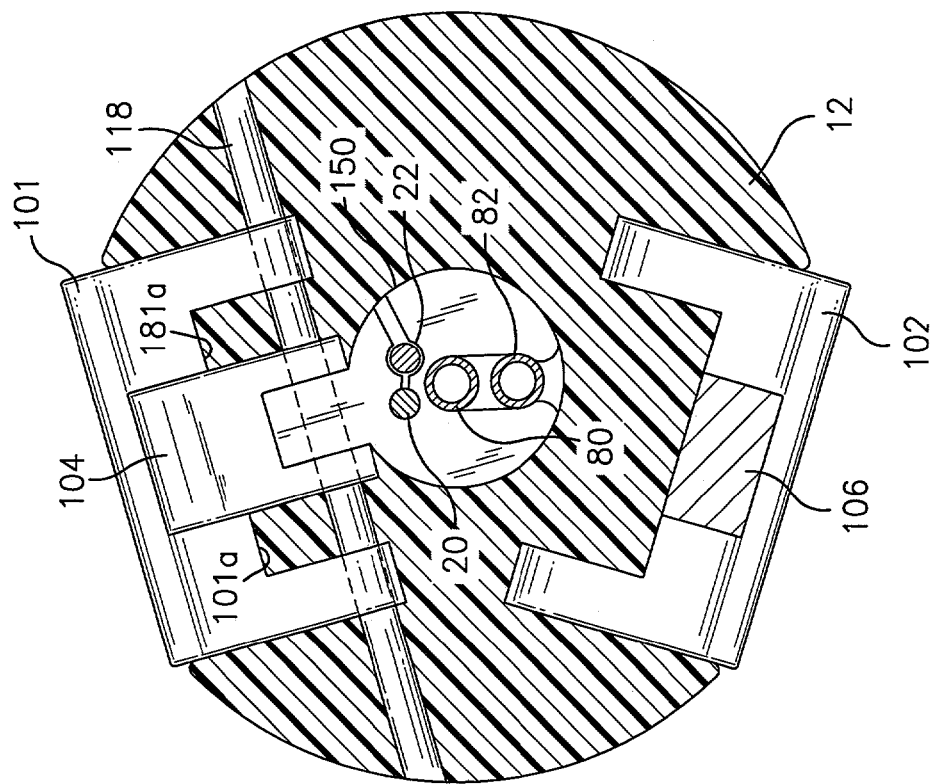
FIG. 3A is a cross-sectional view taken along lines 3A-3A of FIG. 1 showing the engagement of the first link with the distal needle driver.
Figure 3:
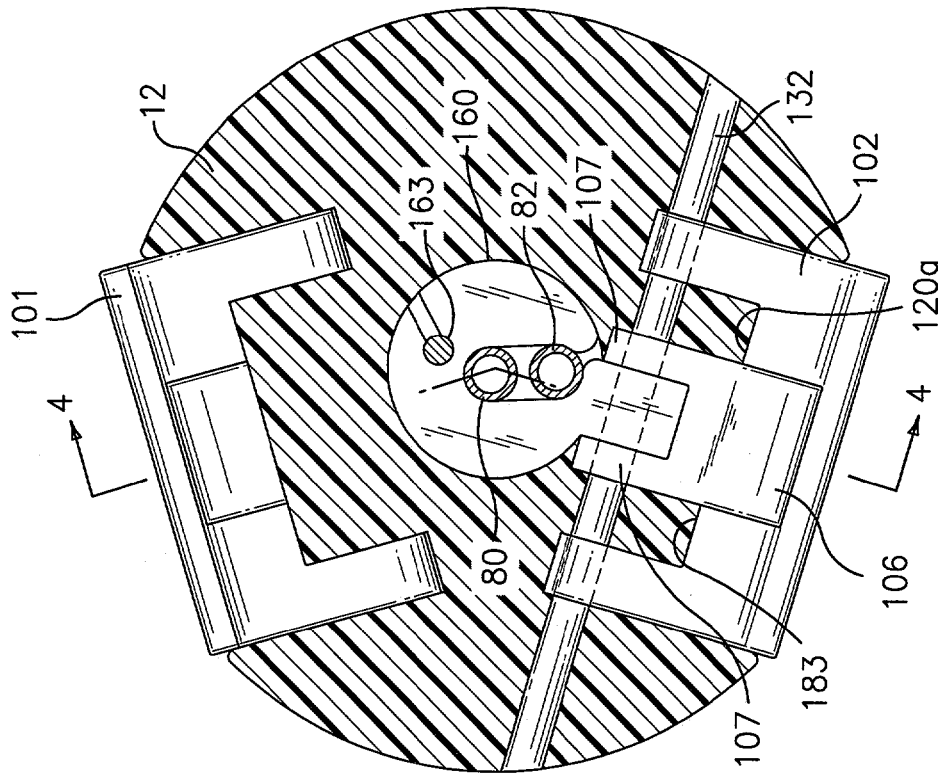
FIG. 3 is a cross-sectional view taken along lines 3-3 of FIG. 1 showing the engagement of the second link and the proximal needle driver of the apparatus.

Turning now to the body portion 12 of apparatus 10 which contains the actuating mechanisms for driving the needles 20, 22, and with initial reference to FIGS. 1 and 2, the body portion 12 includes first and second levers 101, 102 pivotably mounted thereto. The first lever 101 is operatively connected to first needle 20 by link 104 and the second lever 102 is operatively connected to the second needle 22 by link 106. Lever 101 is seated in its initial position within cavity 180a of body portion 12 such that the bottom surface 101a of the lever 101 contacts the planar surface 181 inside the cavity 180a as shown in FIG. 3A. Lever 102 is similarly seated in a cavity 180b (not shown in FIG. 2) such that surface 102a abuts planar surface 183 (see FIG. 3).

The first lever 101 is pivotably mounted to the distal end of body portion 12 by a lever mounting pin 110 extending through distal apertures 108 and through the illustrated openings in the body portion 12. First link 104 is mounted to lever 101 by a link pin 114 extending through apertures 112 in lever 101 and through the distal openings 116 in link 104. The proximal end of link 104 is mounted to tab 154 of distal or first needle driver 150 by a link pin 118 extending through proximal apertures 120 and tab opening 152 of needle driver 150.

Needle driver 150 functions to advance first needle 20 into engagement with ferrule 70. Needle driver 50 is positioned in cavity 13b of body portion 12 and has a first longitudinal opening 153 dimensioned to frictionally mount a proximal portion of first needle 20 such that distal movement of needle driver 50 advances needle 20 distally. Needle driver 50 also has a second longitudinal opening 155, dimensioned slightly larger than the first longitudinal opening 153 and the diameter of the first needle 20, to allow unobstructed passage of second needle 22 therethrough. Consequently, when lever 101 is pivoted from the initial (closed or prefired) position of FIG. 4 to the open (fired) position of FIG. 9, link 104 slides needle driver 150 distally to the position shown in FIG. 9. Note that tab 154 will engage projection 142 of stop 140 (positioned in recess 13a of body portion 12) to limit the distal travel of needle guide 150. As the needle driver 150 is advanced distally, it carries the needle 20 out of the opening 47A in face 46, through window 17 and into engagement with ferrule 70. After engagement of pointed tip 21 of needle 20 with ferrule 70, lever 101 is returned to the initial position of FIG. 4 causing link 104 to slide the distal needle driver 150 back to its initial (proximal) position with the needle 20 retracting the ferrule 70 proximally into face 46 of tubular portion 14.

Figure 4:
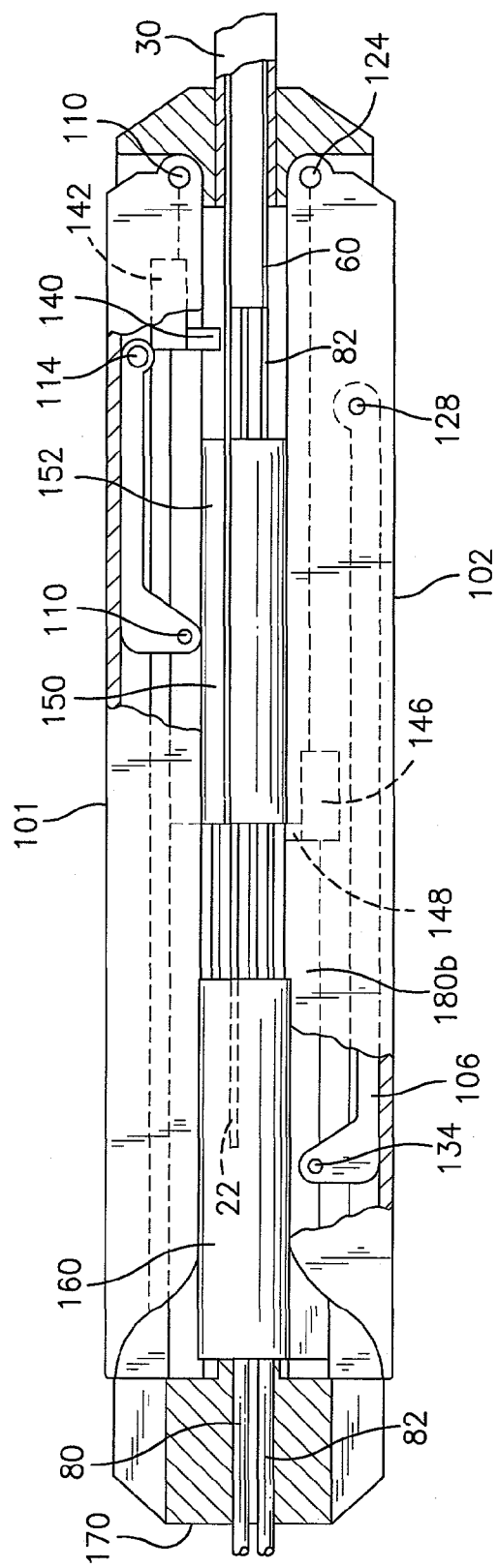
FIG. 4 is a side view, in partial cross-section, of the body portion illustrating the first and second levers in the initial (closed) position.
Figure 4A:
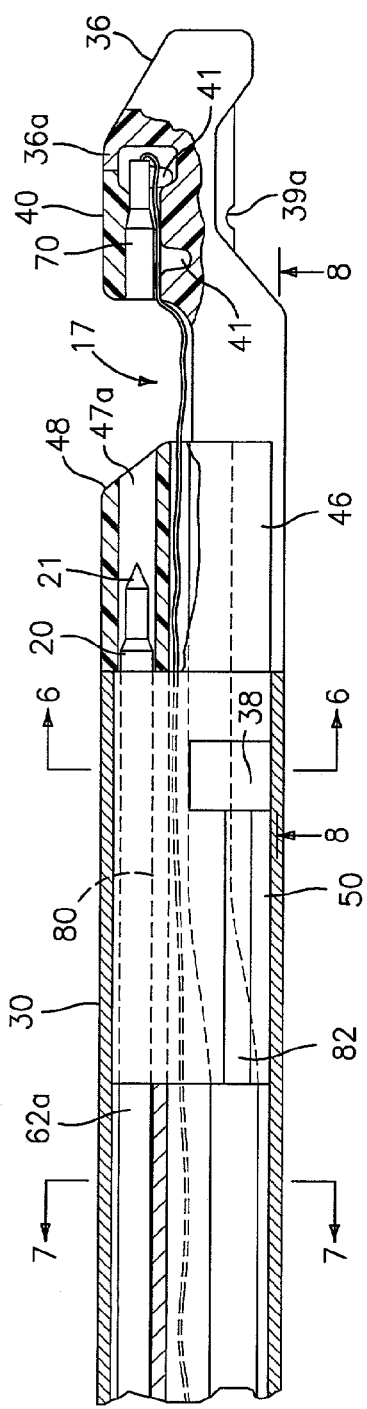
FIG. 4A is a side view, in partial cross-section, of the tubular portion corresponding to the position of the levers in FIG. 4 and illustrating the first needle prior to engagement with its respective ferrule.
Figure 4B:
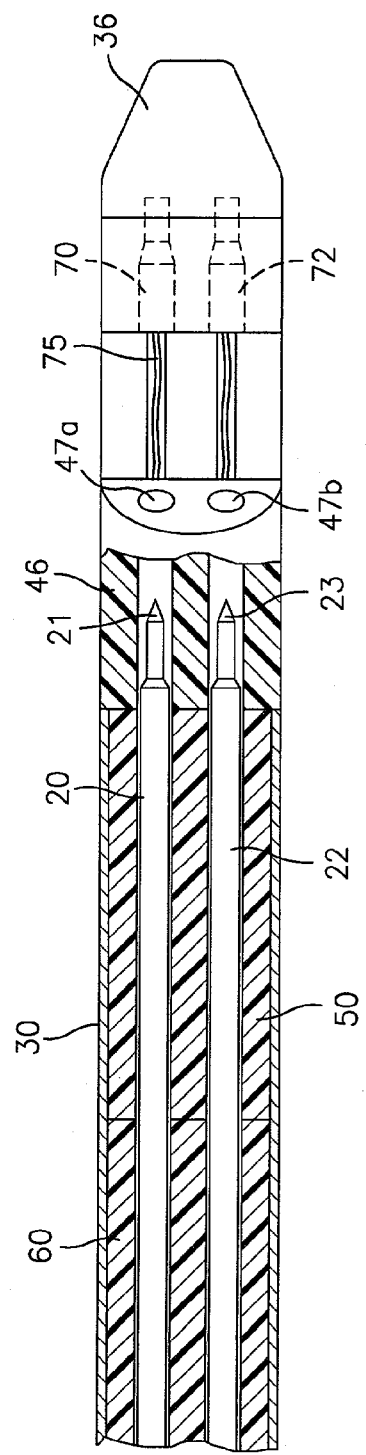
FIG. 4B is a top view, in partial cross-section, of the tubular portion corresponding to the position of the levers in FIG. 4 and illustrating both needles in the retracted position prior to engagement with their respective ferrules.
Figure 5:
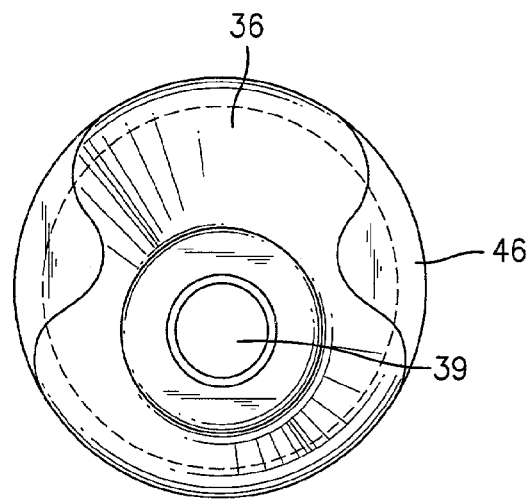
FIG. 5 is a front view of the apparatus of FIG. 1 illustrating the configuration of the tongue.
Figure 6:
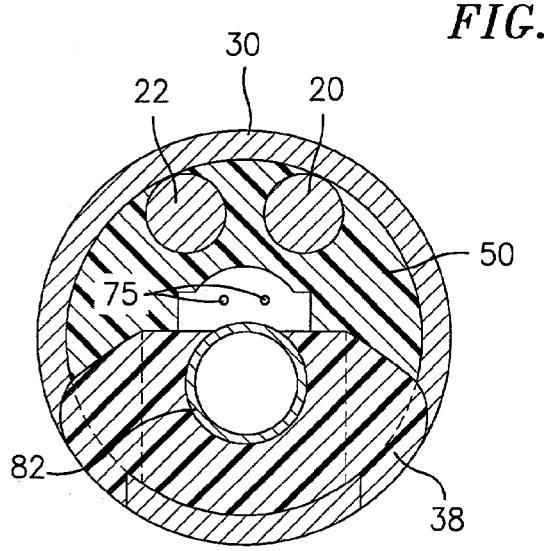
FIG. 6 is a cross-sectional view taken along lines 6-6 of FIG. 4A illustrating the engagement of the tongue and outer tube.
Figure 7:
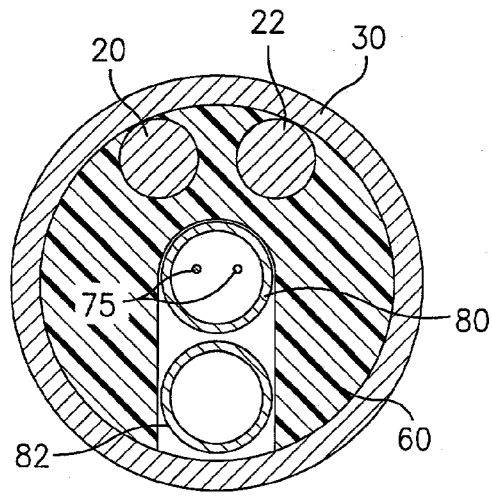
FIG. 7 is a cross-sectional view taken along lines 7-7 of FIG. 4A.
Figure 8:
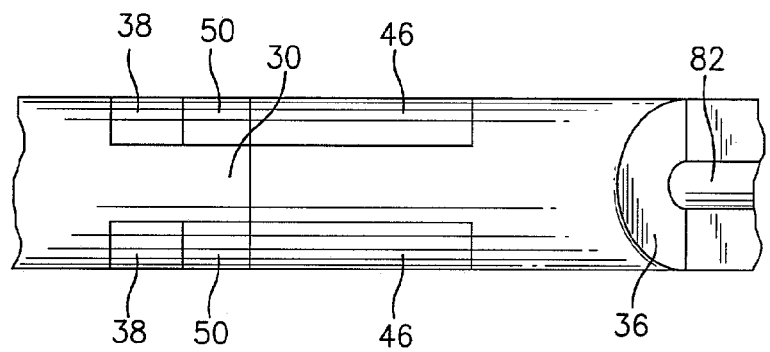
FIG. 8 is a cross-sectional view taken along lines 8-8 of FIG. 4A showing the engagement of the tongue with the face and the outer tube of the apparatus.
Figure 9:
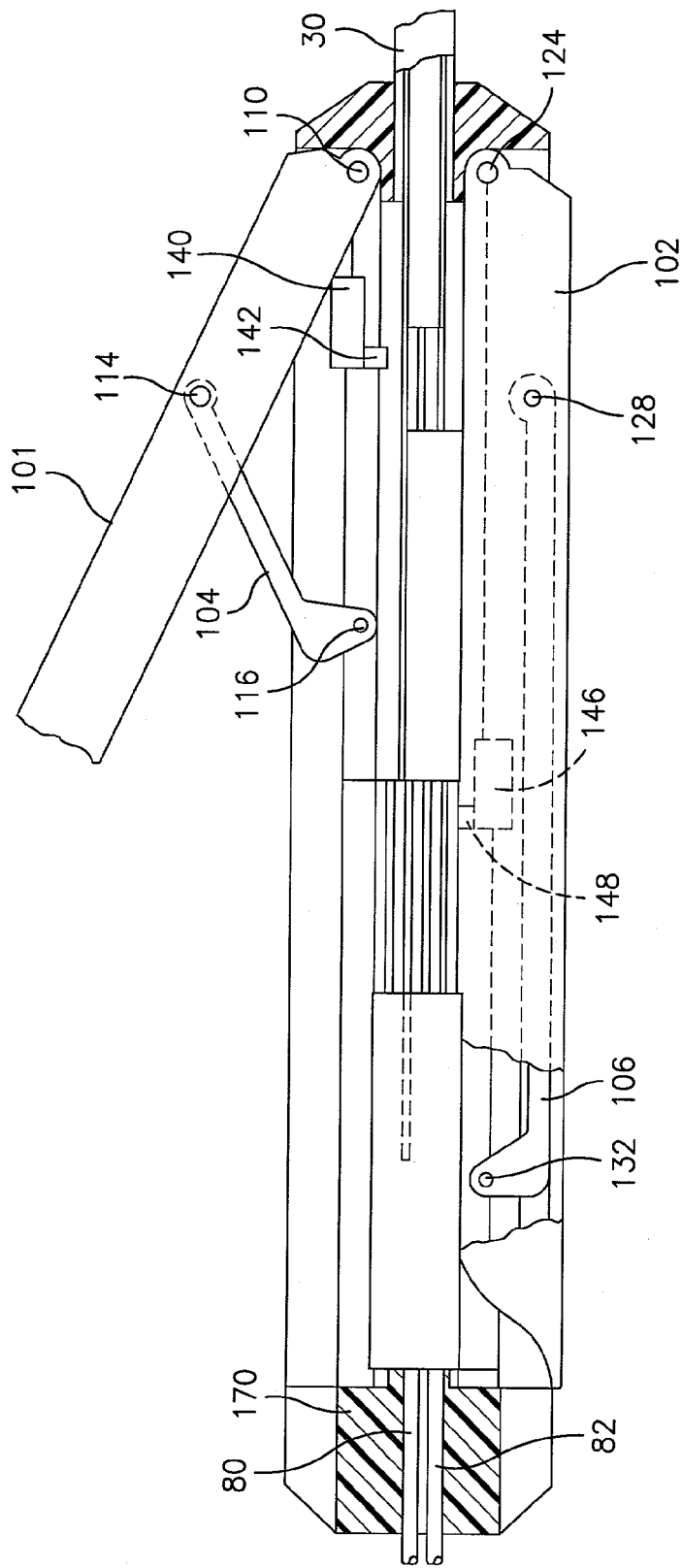
FIG. 9 is a view similar to FIG. 4 illustrating the second lever in the initial position and the first lever in the open position to advance the first needle into engagement with the ferrule.

The second lever 102, as shown in FIGS. 2, 4 and 9, functions in a similar manner to first lever 101 and is designed to advance second needle 22. Distal apertures 122 of lever 102 receive mounting pin 124 to pivotably connect lever to body portion 12. Lever pin 128 connects second link 106 to lever 102 as it extends through apertures 126 in lever 102 and distal openings 130 in link 106. The proximal end of second link 106 is connected to proximal or second needle driver 160 via link pin 132 extending through proximal openings 134 in link 106, aperture 162 in tab 164 of needle driver 160, and through the illustrated openings in body portion 12.

Figure 11:
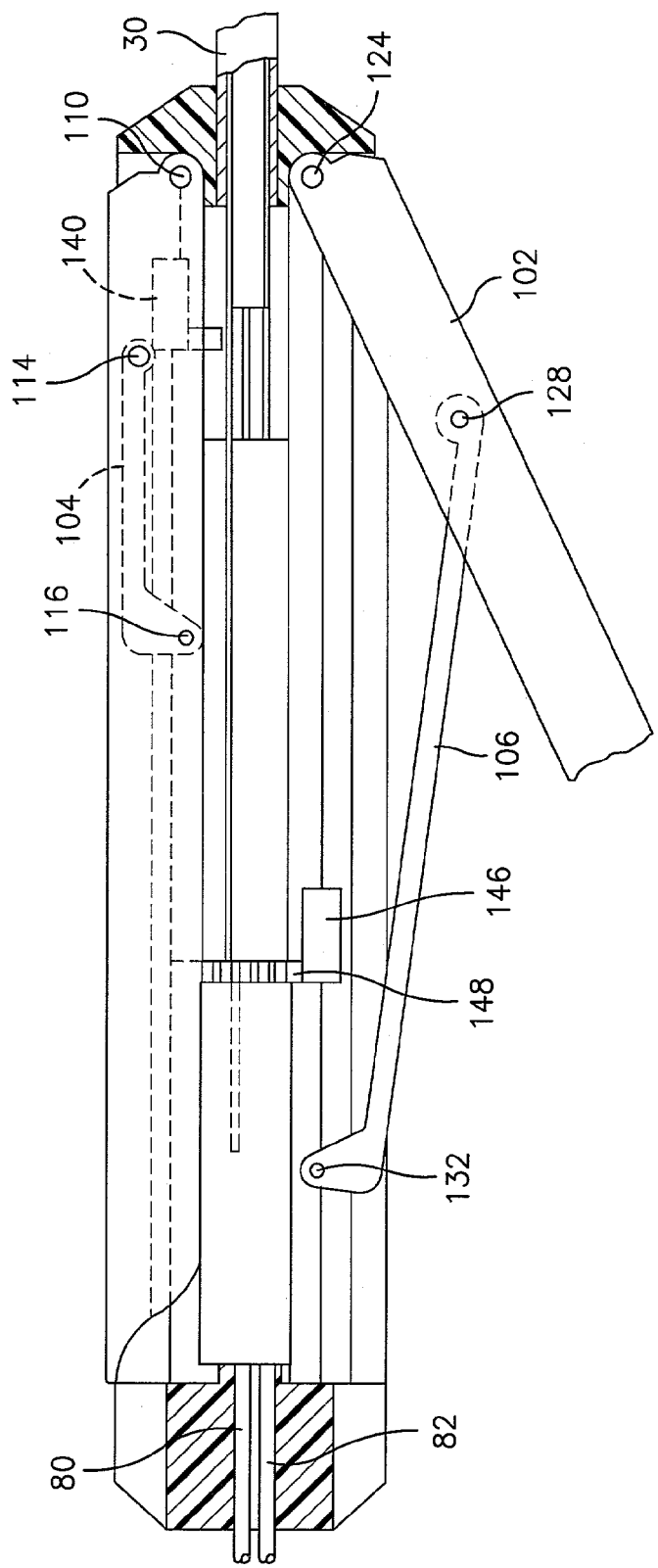
FIG. 11 is a view similar to FIG. 4 illustrating the first lever in the closed position and the second lever in the open position to advance the second needle into engagement with the ferrule.
Figure 13:
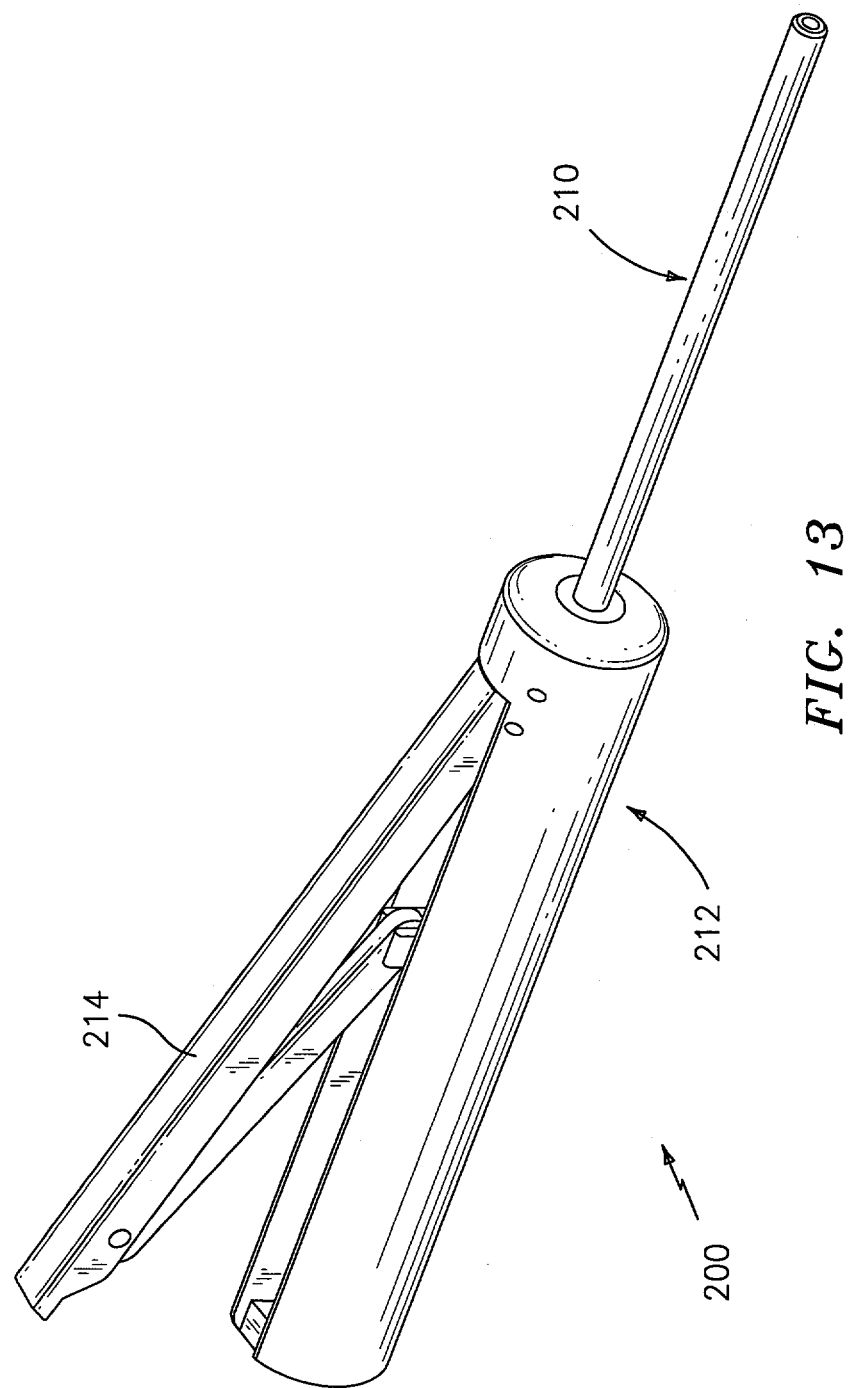
FIG. 13 is a perspective view of the apparatus for crimping the suture securing member.

Proximal needle driver 160 has an opening 163 dimensioned to frictionally mount proximal portion of needle 22. When lever 102 is pivoted from its initial position of FIG. 4 away from body portion 12 to the open position shown in FIG. 11, link 106 will advance proximal needle driver 160 to cause distal advancement of needle 22 through opening 47b in face 46 to engage ferrule 72 (Note that the second needle 22 slides through first longitudinal opening 153 of distal needle driver 150 as discussed above). In this manner, as illustrated in FIG. 11A, pointed tip 23 of needle 22 frictionally engages ferrule 72. Tab 164 of needle driver 160 abuts projection 148 of stop 146 to limit its distal advancement which in turn limits the travel of needle 22. When lever 102 is returned to its initial position of FIG. 4, proximal needle driver 160 is retracted to its original position thereby retracting needle 22 and ferrule 72 back into face 46 through opening 47b.

End cap 170 is mounted on the proximal end of body portion 12 and has recesses 172, 174 configured and dimensioned for receipt of the user's finger to facilitate actuation of first and second levers 101, 102. End cap 170 also includes first opening to allow passage of tube 80 and a second opening to allow passage of tube 82.

Supported within tubular portion 14 and extending through axial bore 103 of body portion 12 and end cap 170, are suture tube 80 and guide wire tube 82. More specifically, tubes 80 and 82 extend through aligned notches 51, 61 of distal and proximal needle guides 50, 60 respectively (see e.g. FIGS. 4A and 7), through notch 156 in distal needle driver 150 and through notch 165 of proximal needle driver 160. Tube 80 is designed to receive the suture 75 to retain it within the apparatus. Tube 82 is configured to receive a guide wire for locating the apparatus 10 during use as will be described below. Additionally, tube 82 can function to transport fluid, such as radiopaque dye, which can be ejected out of opening 36A in tongue 36 (see FIG. 4).

In use, in the initial position, levers 101 and 102 are seated within the respective cavities 180*a*, 180*b* in the body portion 12 as shown in FIG. 4. In this position, links 104 and 106 are substantially parallel to the respective levers 101, 102 and the needle drivers 150, 160 are in the proximal position. When it is desired to advance needle 20 through the body tissue positioned in window 15, lever 101 is pivoted away from body portion 12, thereby moving distal needle driver 150 to a distal position, limited by stop 140, to carry needle 20 distally. Consequently, needle 20 is guided along grooves 62*a*, 52*a* of needle guides 60, 50, exits through opening 47*a* in face 46, and advances through the body tissue into the ferrule holder 40 to engage ferrule 70 as shown in FIG. 9A to pick up one end of suture 75. Lever 101 is then returned to its initial position of FIG. 4, sliding distal needle driver 150 to its proximal position to retract the needle 20 and attached ferrule 70 inside face 46 to the position of FIG. 10, thereby pulling one end of suture 75 through the body tissue.

Subsequently, second lever 102 is pivoted away from body portion 12 to the position of FIG. 11. This moves proximal needle driver 160 to a distal position to advance second needle 22. Second needle 22 is guided in grooves 62*b*, 52*b* of needle guides 60, 50, through opening 47*b* in face 46, and through the body tissue positioned in window 17 into ferrule holder 40 to engage ferrule 72 as shown in FIG. 11A to pick up the other end of suture 75. Lever 102 is returned to the initial position of FIG. 4 to slide proximal needle driver 160 to its original position to retract needle 20 and attached ferrule 72 inside face 46 as shown in FIG. 12. This pulls the second end of suture 75 through the body tissue. It should be appreciated that lever 102 can be actuated before lever 101 if desired.

Turning now to the apparatus 200 for securing the suture 75 applied by apparatus 10, and with initial reference to FIGS. 13-16, apparatus 200 includes a cylindrical body portion 212 and a tubular portion 210 extending from a distal end of the body portion 212 and housing jaw assembly 218 for crimping a suture securing member or connecting sleeve 216 held in the jaws. A lever 214 is pivotably mounted to the body portion 212 and is movable from the initial (open) position illustrated in FIGS. 13 and 15 to a closed position illustrated in FIG. 19 to cam the jaws to a closed position to crimp the suture securing member 216 in the manner described below.

Figure 14:
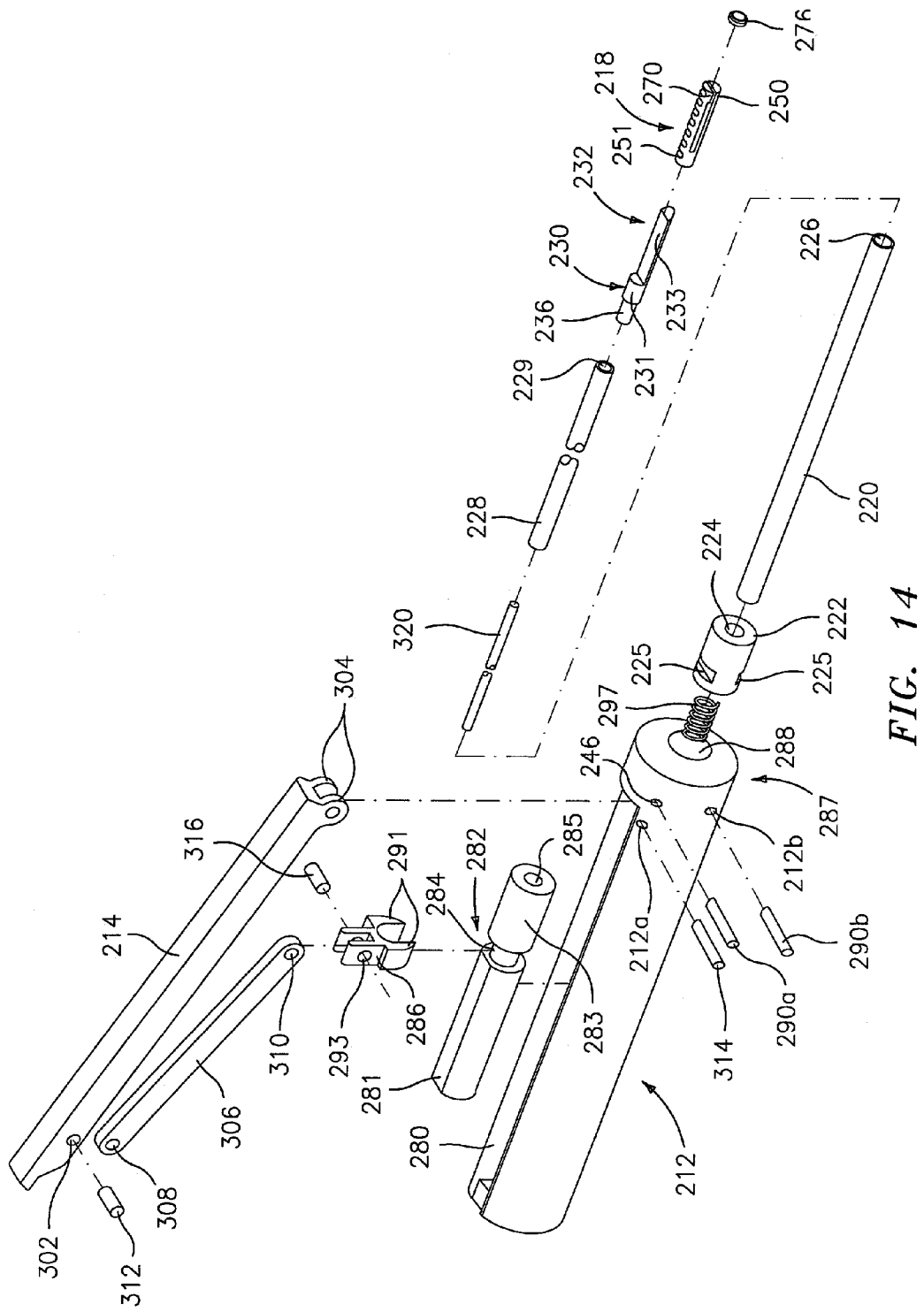
FIG. 14 is an exploded perspective view of the apparatus of FIG. 13.
Figure 19:
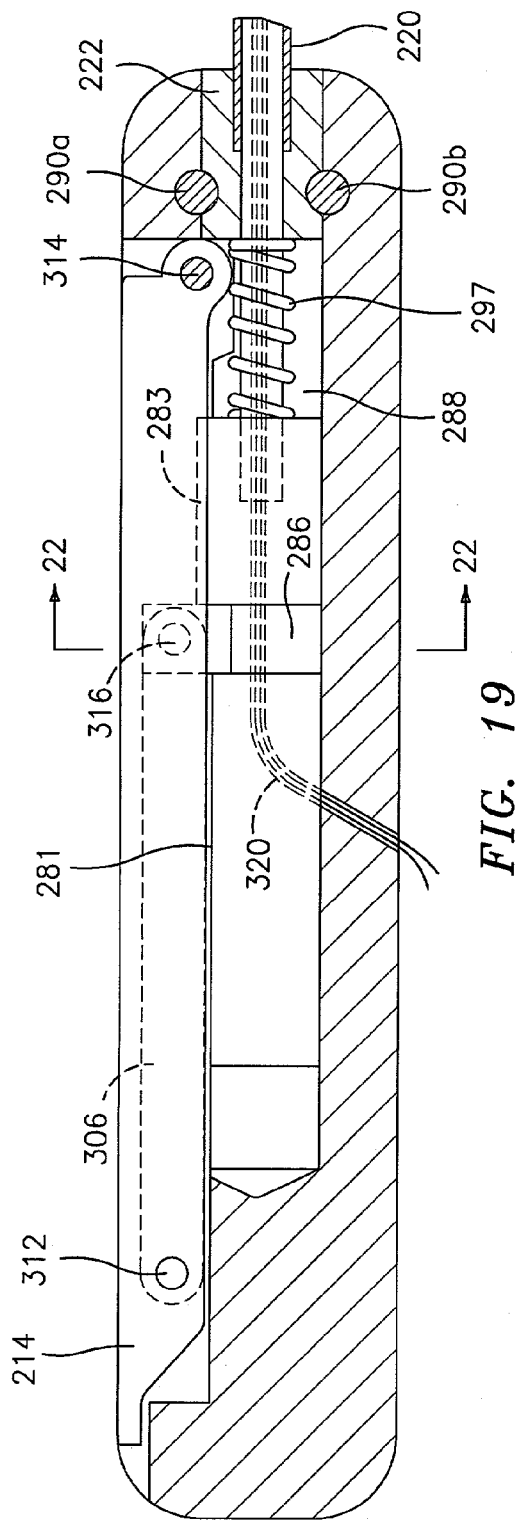
FIG. 19 is a cross-sectional view similar to FIG. 15 illustrating the lever in the closed position to close the jaws.
Figure 20:
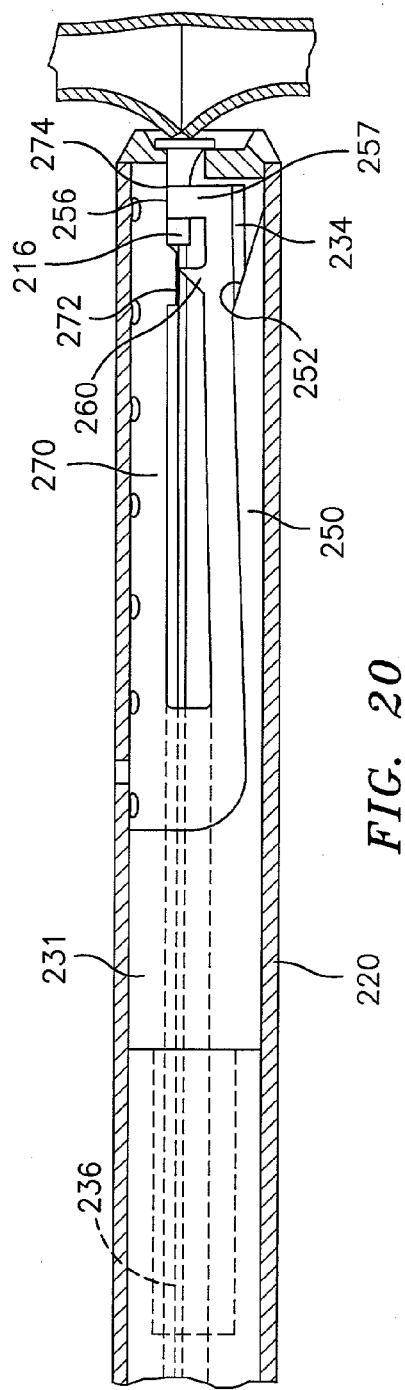
FIG. 20 is a cross-sectional view similar to FIG. 16 corresponding to the position of the lever in FIG. 19 and illustrating the jaws in the closed position to crimp the suture securing member around a suture.

Referring to FIGS. 14-16, tubular portion 210 includes a drive tube 228, a jaw closer 230, a jaw assembly 218 and an outer tube 220. Outer tube 220 is seated within an axial bore 224 of cylindrical tube retainer 222 which is fixedly mounted in the distal end of body portion 212. This retains the outer tube 220 in a fixed position.

Inner or drive tube 228 is received in longitudinal bore 226 of outer tube 220 and is frictionally mounted at its proximal end within axial bore 285 of drive block 282 which is positioned in body portion 212. Thus, drive tube 228 is reciprocated by drive block 282 in the manner described below. Also mounted within outer tube 220 is jaw closer 230. Jaw closer 230 has a proximal mounting rod 236 seated within axial bore 229 of drive tube 228 such that head 231 abuts the distal edge. The jaw closer 230 is moved by the drive tube 228 from a proximal position as shown in FIG. 16 to a distal position as shown in FIG. 18 to move the jaws to the closed position. More specifically, jaw closer 230 has a camming surface 234 at its distal end 232 which engages the underside of lower jaw 250 (as viewed in FIG. 14) to force lower jaw 250 towards upper jaw 270. This is described in more detail below.

Jaw assembly 218, mounted to outer tube 220 by mounting pin 278 (or alternatively brazed into the outer tube), includes a movable jaw 250 and a stationary jaw 270 which are hinged at the proximal end 251 and are spaced apart thereafter to form a gap 253 therebetween. Movable jaw 250, as best shown in FIGS. 16 and 18, has a camming edge 252 on its lower surface (as viewed in FIG. 16) which cooperates with the camming surface 234 of the jaw closer 230. A pair of arms 257 at the distal end form a receiving recess 254 for mounting the suture securing element 216. Stop surface 256 on arm 257 limits the travel of jaw 250 towards jaw 270. Cutting blade 260, positioned proximally of arms 257, is also cammed towards stationary jaw 270 by camming surface 234 and is configured to engage and cut the suture concomitantly with the crimping of the suture securing member 216.

Stationary jaw 270 has an abutment surface 274 which cooperates with stop surface 256 of movable jaw 250 to limit travel thereof. Backstop 272 facilitates cutting of the suture when contacted by cutting blade 260.

Figure 21:
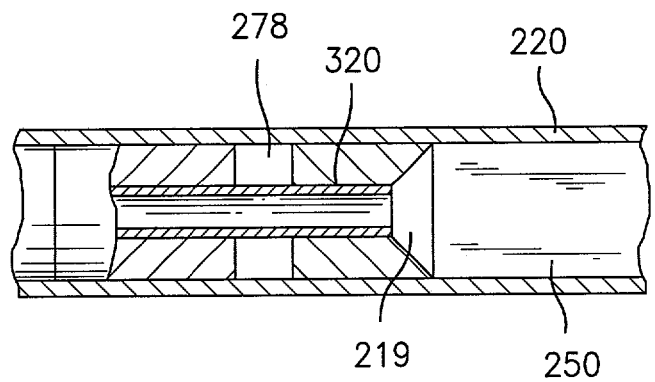
FIG. 21 is a cross-sectional view taken along lines 21-21 of FIG. 16 showing the positioning of the suture tube.

Jaw assembly 218 has a conically shaped proximal end 219, best shown in FIG. 21, to mount suture tube 320. This conical shape facilitates threading of the suture through the instrument as described below. Suture tube 320 extends through axial bore 229 of drive tube 228 and through central bore 288 of body portion 212, exiting through a side portion as shown in FIG. 15.

An end cap 276 is mounted at the distal end of the jaw assembly 218 and has an opening to enable loading and removal of the suture securing member 216. The suture securing member 216, as shown in FIG. 17 has a cylindrical tubular portion 240 dimensioned for reception in receiving recess 254 of arms 257. Head 244 is designed to abut the sutured tissue. Examples of alternate configurations for the suture securing member are disclosed in pending U.S. application Ser. No. 08/201,864, filed Feb. 24, 1994, the contents of which are incorporated herein by reference.

Figure 22:
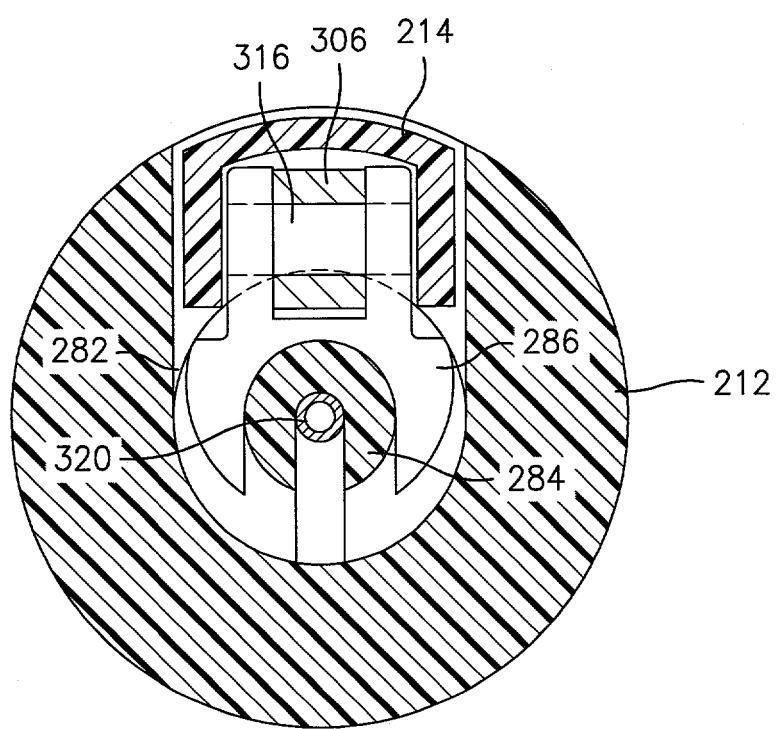
FIG. 22 is a cross-sectional view taken along lines 22-22 of FIG. 19 illustrating the engagement of the collar with the drive block of the apparatus.
Figure 23:
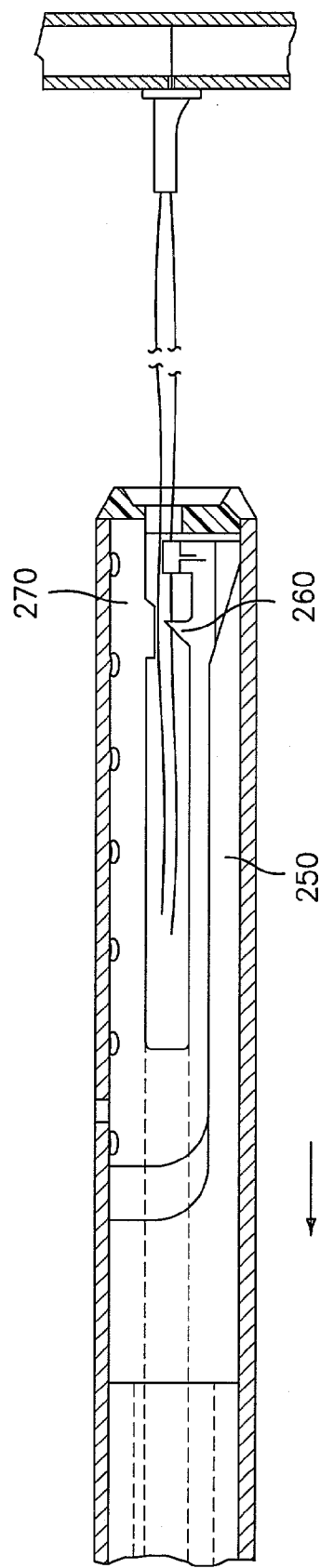
FIG. 23 is a cross-sectional view similar to FIG. 20 showing the suture securing member crimped on a suture and the apparatus being withdrawn from the surgical site.
Figure 27:
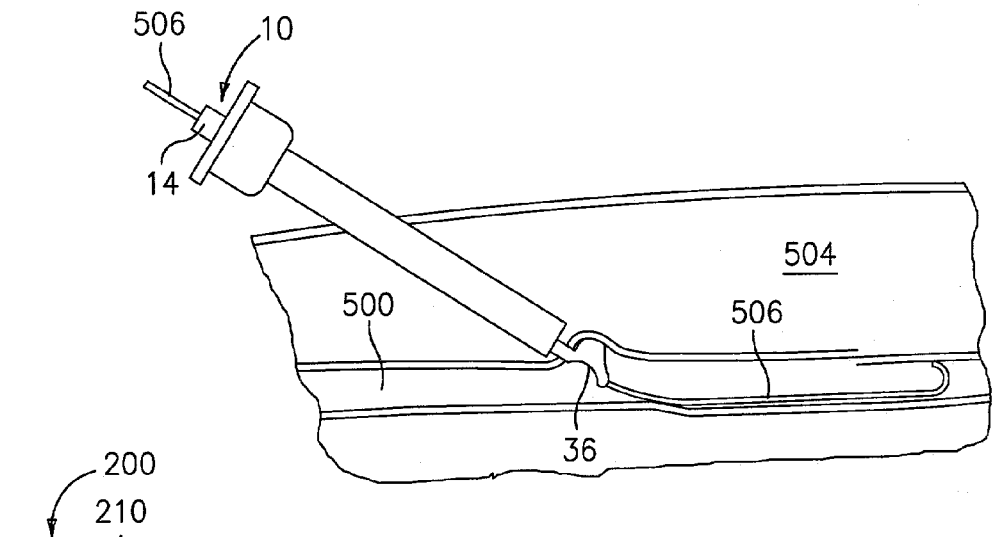
FIG. 27 is a cross-sectional view of a blood vessel and surrounding tissue illustrating the surgical suturing apparatus of FIG. 1 passing through a cannula and applying a suture adjacent the superior side of the vessel puncture wound.

Turning now to the body portion 212 of apparatus 200, and with reference to FIGS. 14 and 15, drive block 282, biased proximally by spring 297, is seated within central bore 288 and as mentioned above has an opening 285 to frictionally receive the proximal end of drive tube 228. Proximal of head portion 283 is a recessed area, defined by reduced diameter rod portion 284, for mounting locking collar 286. More particularly, spaced apart fingers 291 of locking collar 286 straddle rod portion 284 as best shown in FIG. 22. Locking collar 286 operatively connects the lever 214 and link 306 to the drive block 282.

Lever 214 is mounted at its distal end to body portion 212 via lever pin 314 extending through distal apertures 304 and through openings 246 in the body portion 212. Lever 214 is connected at its proximal end to link 306 via link pin 312 extending through apertures 308 and 302. The distal end of link 306 is seated in locking collar 286 such that collar pin 316 extends through aperture 310 in link 306 and through apertures 293 in the locking collar 286. As shown, in the initial position of FIG. 15, lever 214 extends at an angle to the longitudinal axis of body portion 212. When the lever 214 is pivoted to the closed position of FIG. 19 to actuate the instrument, it moves into recess 280 (FIG. 14) in body portion 212 and buts planar surface 281 of drive block 282.

Body pins 290A and 290B extend through openings 212a, 212b in the body portion 212 to engage slots 225 formed in tube retainer 222. This holds tube retainer 222 fixed with respect to body portion 212.

As can be illustrated, lever 214 is connected to the locking collar 286 via link 306. Locking collar 286, in turn, straddles drive block 282 which mounts drive tube 228. Drive tube 228 mounts jaw closer 230. Consequently, movement of lever 214 to its closed position slides locking collar 286, drive block 282, drive tube 228, and jaw closer 230 distally to cam the jaws to the closed position. Outer tube 220 and jaw assembly 218 remain fixed during this movement as outer tube 220 is mounted to fixed tube retainer 222 and jaw assembly 218 is mounted to stationary outer tube 220.

In use, in the initial (prefired) position of FIG. 15, lever 214 is positioned at an angle to the longitudinal axis of body portion 212, spaced from recess 280, such that locking collar 286 and drive tube 282 are in the proximal position (biased by spring 297). Thus, drive tube 228 and jaw closer 230 are also in the proximal position such that camming surface 234 of closer 230 is spaced from the cooperating camming edge 252 of movable jaw 250 (see FIG. 16). When it is desired to crimp the suture securing member 216 positioned in arms 257 between movable jaw 250 and stationary jaw 270, lever 214 is moved towards body portion 212 and into receiving recess 280. This slides the locking collar 286 and drive block 282 distally against the force of spring 297 to the position shown in FIG. 19. This longitudinal translation of the drive block 282 slides the drive tube 228 and jaw closer 230 distally to cause the camming surface 234 to engage camming edge 252 of movable jaw 250 to force the movable jaw 250 towards stationary jaw 270 (see FIG. 20). This crimps the suture securing member 216 between the jaws 250, 270. As the movable jaw 250 is moved to the closed position, cutting blade 260 contacts and cuts the suture against the backstop 272 of stationary jaw 270. When pressure on lever 214 released, lever 214 returns to its open position and drive tube 228 returns to its proximal position under the force of spring 297.

FIGS. 17 and 18 illustrate the suture securing member 216 being manually loaded through end cap 276 into the apparatus 200. As shown, the suture securing member 216 is seated within receiving recess 254 between arms 257 of the movable jaw 250. It should be understood that alternatively, apparatus 200 can be provided with the suture securing member preloaded in the apparatus.

Referring now to FIGS. 23-29, a preferred method of dosing a puncture in a blood vessel is disclosed. FIG. 24 illustrates guide wire 506 passing extracorporeally through tissue 504 and puncture 502 in vessel 500. Vessel 500 is typically the femoral artery, wherein puncture 502 was created to access the circulatory system to perform, for example, an angioplasty or angiography procedure. External pressure (indicated by arrow X) can be applied to reduce or eliminate blood flow through puncture 502. As shown and described herein, the distal end of guide wire 506 is directed towards the torso of the patient.

Turning to FIG. 25, cannula 508 and obturator assembly 509 have been inserted such that the distal end of the cannula 508 is disposed substantially adjacent puncture 502. Obturator assembly 509 preferably includes flexible outer sleeve 510 having a lumen through which passes flexible tubular member 512. Alternately, sleeve 510 and tubular member 512 can be combined into one unit with two channels. Tubular member 512 also has a lumen passing therethrough which is sized to receive guide wire 506. In use, guide wire 506 is used to direct the cannula and obturator assembly to puncture 502. The proximal end of obturator assembly has valve assembly 516 having fittings 518 and 520 in communication therewith. Guide wire 506 passes through fitting 520 while fitting 518 is in fluid communication with outer sleeve 510. As best seen in FIG. 25A, sleeve 510 has aspiration port 514 that is disposed within vessel 500 when the obturator assembly is placed in a desired position. Fluid communication between orifice 514 and fitting 518 allows for blood aspiration to positively indicate proper positioning of cannula 508 and for the injection of fluids into vessel 500, if desired.

After cannula 508 has been properly placed, obturator assembly 509 is slid off guide wire 506 and the previously described surgical suturing apparatus 10 is threaded over the guide wire by passing the guide wire through opening 39 in tongue 36 (see, for example, FIG. 5) and through instrument 10. The suturing instrument can then be directed through cannula 508. Tongue 36 at the distal end of apparatus 10 is passed through puncture 502 such that vessel tissue adjacent the puncture is disposed in window 15, between tongue 36 and face 46 of apparatus 10. Lever 101 (not shown) can then be manipulated as previously described to draw a ferrule and suture through the vessel. As shown, a preferred method is to first direct a suture through the inferior side of the puncture. The suturing device can then be rotated to the other side of puncture 502, i.e., the superior side, and lever 102 (not shown) can be manipulated to draw the second ferrule and suture through the vessel. After application of the suture, instrument 10 is withdrawn from cannula 508, leaving suture 75 behind.

Figure 28:
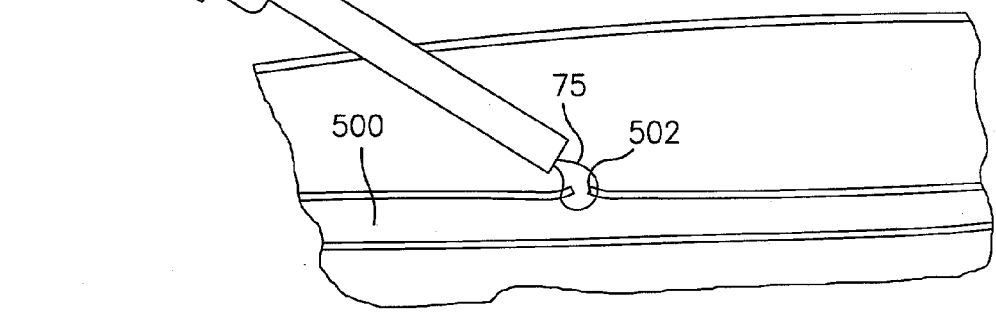
FIG. 28 is a cross-sectional view of a blood vessel and surrounding tissue with a suture applied across a puncture in the vessel and further illustrating the distal end of the suture securing device of FIG. 13 with the suture passing therethrough.
Figure 29:
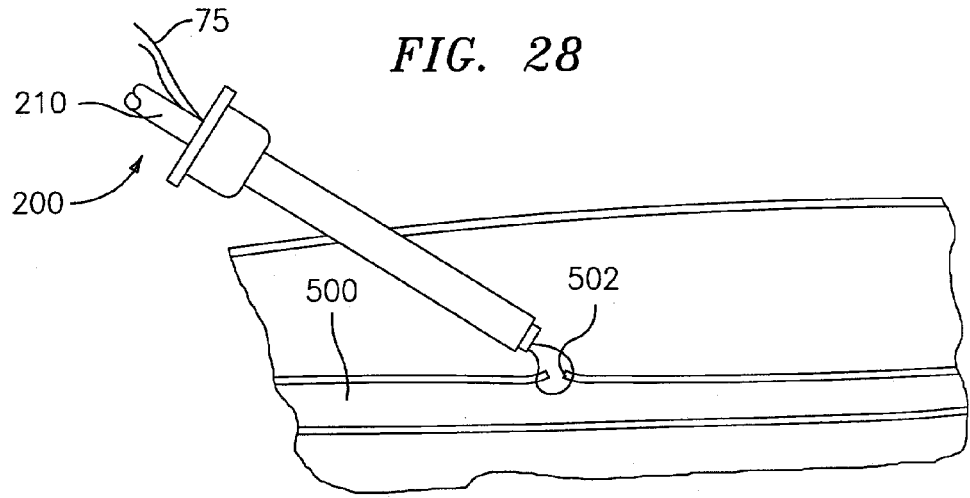
FIG. 29 is similar to FIG. 28 with the suture securing device passing through the cannula and approaching the vessel puncture; and, FIG. 30 is a surgical kit including a cannula and obturator assembly, a suturing device and a suture securing device.

Turning to FIGS. 28-29, a preferred method for tightening and securing suture 75 to close puncture 502 is illustrated. The loose ends of suture 75 are threaded through the distal end of a suture securing device, such as device 200 shown and previously described with respect to FIGS. 13-23. As shown in FIG. 29, device 200 with the suture passing therethrough is introduced into cannula 508. The suture is pulled tight (FIGS. 18 and 20), and lever 214 of device 200 is actuated to simultaneously crimp a securing member and cut suture 75. Device 200 and cannula 508 can then be removed and a topical bandage applied.

Figure 30:
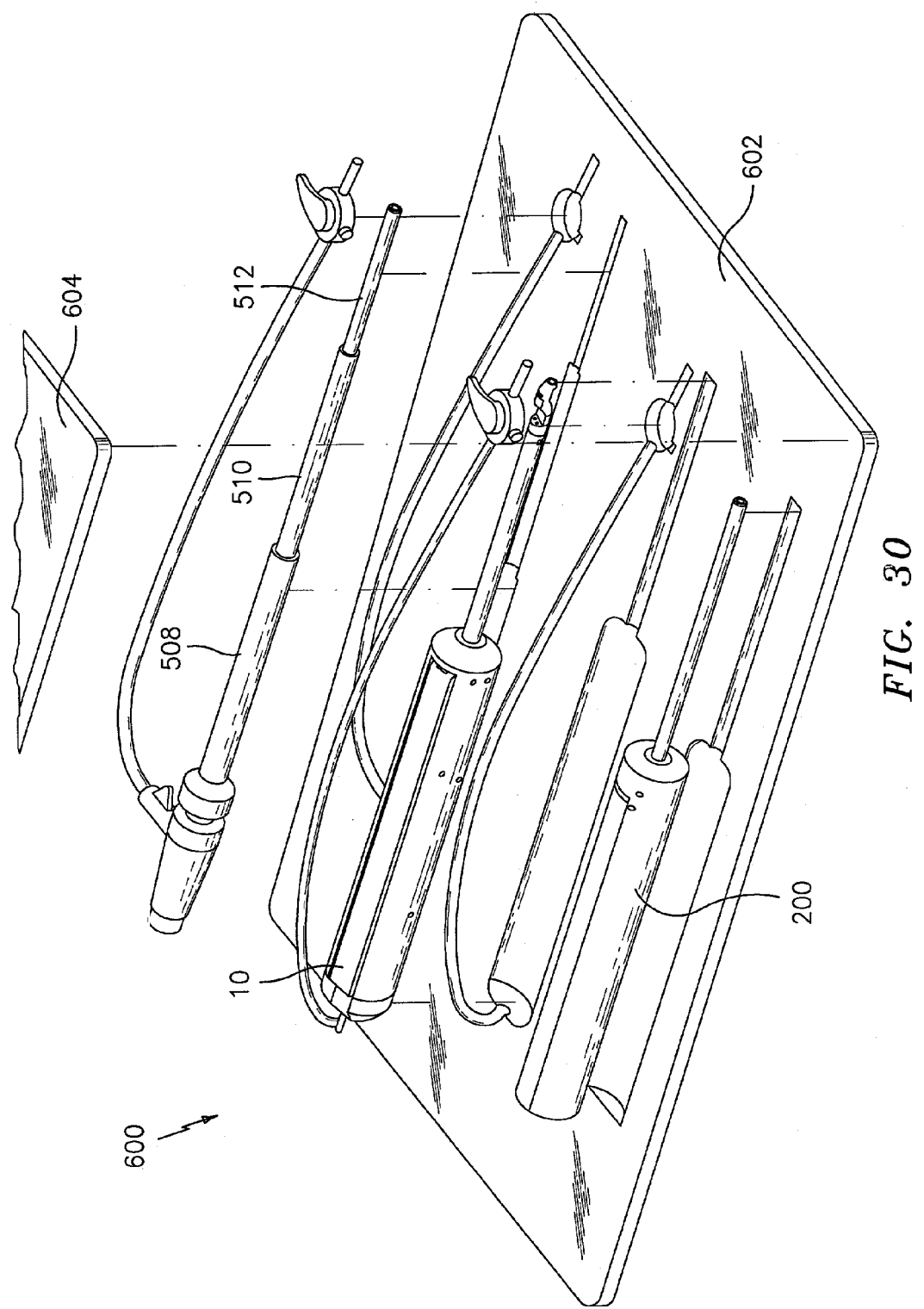

FIG. 30 illustrates a surgical kit 600 useful for dosing a puncture in a blood vessel. The kit preferably includes suturing device 10, suture crimping device 200, cannula 508 and an obturator assembly including two coaxial flexible tubular members 510, 512. The kit packaging can be at least partially fabricated from thermoformed plastic 602 fabricated from polyethylene fibers, (such as TYVEK* available from Dupont) to facilitate sterilization.

It will be understood that various modifications can be made to the embodiments disclosed herein. Therefore, the above description should not be construed as limiting but merely as examples of preferred embodiments. Those skilled in the art will envision other modifications.

What is claimed is:

1. A surgical apparatus comprising a tip, the tip having a longitudinal axis, a distal end, and a proximal end, the tip further comprising:
   a window for receiving tissue;
   a first wall at a proximal end of the window, the first wall disposed at an angle to the longitudinal axis, the angle selected to impede insertion of the tip into a wound; and,
   a second wall disposed at an angle to the longitudinal axis at a distal end of the window, further comprising a ferrule holder, the ferrule holder including the second wall, further comprising a tongue extending between the first and second walls, wherein the ferrule holder includes projections receivable within grooves of the tongue for retaining the ferrule holder on the tongue.

2. A surgical apparatus in accordance with claim 1, the surgical apparatus further comprising:
an elongate body assembly connecting a body portion to the tongue member, and further comprising first and second elongate needles positioned at least partially within the elongate body assembly, said first needle being longitudinally movable by a first lever and said second needle being longitudinally movable by a second lever.

3. The surgical apparatus of claim 2 wherein said first and said second levers are spaced apart less than 180 degrees from each other.

4. The surgical apparatus of claim 2 wherein said first and said second levers are not diametrically positioned.

5. The surgical apparatus of claim 2 wherein the first and second elongate needles are eccentrically positioned within the elongate body assembly.

6. A surgical apparatus in accordance with claim 1, the surgical apparatus further comprising:
a body portion having first and second levers pivotally secured to the body portion, wherein the first lever is a first color to indicate its connection with a first needle, and the second lever is a second color, different than the first color, to indicate its connection with a second needle.

7. A surgical apparatus in accordance with claim 1, the surgical apparatus further comprising
a body portion having first and second levers pivotally secured to the body portion, wherein the first and second levers are mounted to a distal end of the body portion.

8. The surgical apparatus of claim 1, further comprising:
a body portion having a distal end and a proximal end;
a tubular portion having a distal end and a proximal end, the proximal end of the tubular portion attached to the distal end of the body portion, a distal end of the tubular portion positioned proximally of said window; and
a lever having a distal end and a proximal end, the distal end of the lever operatively coupled to the distal end of the body portion, wherein the body portion includes a longitudinal axis and the lever includes a longitudinal axis, and further wherein the longitudinal axis of the lever is parallel to the longitudinal axis of the body portion in a closed position of the lever.

9. The surgical apparatus of claim 8 wherein the lever is actuable to a position where the longitudinal axis of the lever is askew from the longitudinal axis of the body portion.

10. The surgical apparatus of claim 1, further comprising:
a body portion having a distal end and a proximal end;
a tubular portion having a distal end and a proximal end, the proximal end of the tubular portion attached to the distal end of the body portion, a distal end of the tubular portion positioned proximally of said window; and,
a lever having a distal end and a proximal end, the distal end of the lever operatively coupled to the distal end of the body portion, wherein the lever is pivotally mounted to the body portion, further comprising a link connected at a first end to the lever and at a second end to a slidable member within the body portion.

11. The surgical apparatus of claim 10 wherein movement of the proximal end of the lever towards the proximal end of the body portion forces the slidable member to move towards the distal end of the body portion.

12. The surgical apparatus of claim 11 further comprising a drive block, wherein the slidable member cooperates with the drive block to move the drive block correspondingly with the slidable member.

13. The surgical apparatus of claim 12 wherein the slidable member is a locking collar which surrounds a reduced diameter portion of the drive block.

14. The surgical apparatus of claim 12 wherein the drive block is biased proximally by a spring.

15. The surgical apparatus of claim 12 wherein the drive block includes a longitudinal opening for frictionally receiving a proximal end of a drive tube.

16. The surgical apparatus of claim 11 wherein the proximal end of the lever is biased away from the proximal end of the body portion.

17. The surgical apparatus of claim 10 wherein movement of the proximal end of the lever away from the proximal end of the body portion forces the slidable member to move towards the distal end of the body portion.

18. The surgical apparatus of claim 17 wherein the slidable member is a needle driver.

19. The surgical apparatus of claim 18 further comprising a needle in the tubular portion, the needle movable in response to movement of the needle driver.

20. The surgical apparatus of claim 18 wherein the lever is a first lever, the link is a first link, and the needle driver is a first needle driver, the surgical apparatus further comprising a second lever having a proximal end and a distal end, the distal end of the second lever operatively coupled to the distal end of the body portion, a second link connected at a first end to the second lever and at a second end to a second needle driver within the body portion.

21. The surgical apparatus of claim 20 wherein the second needle driver is positioned proximal to the first needle driver.

22. The surgical apparatus of claim 21 wherein first needle driver receives a first needle, and the first needle driver has a longitudinal opening dimensioned to allow a second needle to pass through the first needle driver freely to the second needle driver.

23. The surgical apparatus of claim 22 wherein the second needle driver receives the second needle.

24. The surgical apparatus of claim 23 wherein the second needle driver includes an opening dimensioned to frictionally receive the second needle, the opening for receiving the second needle being smaller than the longitudinal opening in the first needle driver for passing the second needle.

25. The surgical apparatus of claim 21 wherein the first needle driver includes another longitudinal opening dimensioned to frictionally receive the first needle, wherein the longitudinal opening receiving the first needle is smaller than the longitudinal opening for passing the second needle.

26. The surgical apparatus of claim 10 wherein the slidable member includes a tab with a hole, the second end of the lever surrounding the tab and connected to the tab via a link pin inserted through the hole and through the second end of the lever.

27. A surgical apparatus in accordance with claim 1, the surgical apparatus further comprising:
a body portion having a distal end and a proximal end;
a tubular portion having a distal end and a proximal end, the proximal end of the tubular portion attached to the distal end of the body portion; and,
a lever having a distal end and a proximal end, the distal end of the lever operatively coupled to the distal end of the body portion, wherein the lever is a first lever, the surgical apparatus further comprising a second lever having a proximal end and a distal end, the distal end of the second lever operatively coupled to the distal end of the body portion.

28. The surgical apparatus of claim 27 wherein the second lever is angularly displaced on the body portion from the first lever.

29. The surgical apparatus of claim 28 wherein the second lever is placed less than 180 degrees from the first lever.

30. The surgical apparatus of claim 27 wherein the first lever includes a first color and the second lever includes a second color, different than the first color.

31. The surgical apparatus of claim 1 wherein the tongue includes a lip which wraps around a distal end of the ferrule holder for further retaining the ferrule holder on the tongue.

\* \* \* \* \*